(12) United States Patent
Fujimoto et al.

(10) Patent No.: US 9,567,303 B2
(45) Date of Patent: Feb. 14, 2017

(54) CRYSTAL OF 5-HYDROXY-1H-IMIDAZOLE-4-CARBOXAMIDE HYDRATE AND PHARMACEUTICAL COMPOSITION THEREOF

(71) Applicant: FUJIFILM Corporation, Tokyo (JP)

(72) Inventors: Taisuke Fujimoto, Toyama (JP); Tomohiro Hashimoto, Toyama (JP); Katsuyuki Hayashi, Toyama (JP); Tomoyuki Tanaka, Toyama (JP)

(73) Assignee: FUJIFILM Corporation, Tokyo (JP)

( * ) Notice: Subject to any disclaimer, the term of this patent is extended or adjusted under 35 U.S.C. 154(b) by 34 days.

(21) Appl. No.: 14/796,602

(22) Filed: Jul. 10, 2015

(65) Prior Publication Data

US 2015/0315156 A1    Nov. 5, 2015

Related U.S. Application Data

(60) Division of application No. 14/226,364, filed on Mar. 26, 2014, now Pat. No. 9,108,928, which is a continuation of application No. PCT/JP2012/075106, filed on Sep. 28, 2012.

(30) Foreign Application Priority Data

Sep. 28, 2011 (JP) ................. 2011-213500
Sep. 28, 2011 (JP) ................. 2011-213501

(51) Int. Cl.
C07D 233/90 (2006.01)
A61K 31/4164 (2006.01)
(52) U.S. Cl.
CPC ......... C07D 233/90 (2013.01); A61K 31/4164 (2013.01)
(58) Field of Classification Search
CPC ................... C07D 233/90; A61K 31/4164
See application file for complete search history.

(56) References Cited

U.S. PATENT DOCUMENTS

| 4,503,235 A | 3/1985 | Cook et al. |
| 5,567,816 A | 10/1996 | Schloemer et al. |
| 8,664,405 B2 * | 3/2014 | Kato ............ C07D 233/90 548/323.1 |
| 2004/0102505 A1 | 5/2004 | Merkle et al. |
| 2010/0210855 A1 | 8/2010 | Nobuo et al. |
| 2014/0275568 A1 | 9/2014 | Fujimoto et al. |
| 2015/0315156 A1 | 11/2015 | Fujimoto et al. |

FOREIGN PATENT DOCUMENTS

| EP | 0 159 777 A1 | 10/1985 | |
| JP | 56-25165 A | 3/1981 | |
| JP | 58-24569 A | 2/1983 | |
| JP | 58024569 A * | 2/1983 | |
| JP | 59-170075 A | 9/1984 | |
| JP | 60-185727 A | 9/1985 | |
| JP | EP 0159777 A1 * | 10/1985 | ........... A61K 9/2013 |
| JP | 8-53451 A | 2/1996 | |
| JP | 2002-265601 A | 9/2002 | |
| JP | 2004-509948 A | 4/2004 | |
| JP | WO 2009035168 A1 * | 3/2009 | ........... C07D 233/90 |
| JP | 5726830 B2 | 4/2015 | |
| WO | WO 2009/035168 A1 | 3/2009 | |

OTHER PUBLICATIONS

Chinese Office Action dated Jan. 12, 2015, for Chinese Application No. 201280047308.0 with the partial English translation.
Extended European Search Report dated Dec. 12, 2014, issued in corresponding European Patent Application No. 12835728.2.
International Search Report, issued in PCT/JP2012/075106, dated, Oct. 23, 2012.
Japanese Office Action dated Aug. 12, 2014, issued in corresponding Japanese Patent Application No. 2012-217331.
Japanese Office Action dated Nov. 11, 2014, issued in Japanese Patent Application No. 2012-217331.
Miller et al., Substituted Imidazoles as Precursors of the Purines, Journal of American Chemical Society (J. Am. Chem. Soc.), 1952, vol. 74, pp. 2892-2894.
Non-Final Office Action dated Sep. 12, 2014, issued in U.S. Appl. No. 14/226,364.
Notice of Allowance dated Apr. 13, 2015, issued in U.S. Appl. No. 14/226,364.
Written Opinion of the International Searching Authority, issued in PCT/JP2012/075106, dated, Oct. 23, 2012.
Japanese Office Action dated Dec. 8, 2015, issued in correpsonding Japanese Patent Application No. 2015-025526 (machine translation).
Taiwanese Office Action dated Mar. 1, 2016, issued in Taiwanese Patent Application No. 101135795.

* cited by examiner

*Primary Examiner* — Joseph Kosack
*Assistant Examiner* — Amanda L Aguirre
(74) *Attorney, Agent, or Firm* — Birch, Stewart, Kolasch & Birch, LLP

(57) ABSTRACT

Provided is a method for producing 5-hydroxy-1H-imidazole-4-carboxamide.3/4 hydrate, including:

reacting 2-aminomalonamide with a compound represented by the following formula [1] in the presence of a carboxylic acid to obtain 5-hydroxy-1H-imidazole-4-carboxamide:

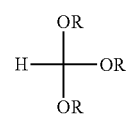

[1]

wherein, in formula [1], each R independently represents a $C_{1-3}$ alkyl group;
reacting the resulting 5-hydroxy-1H-imidazole-4-carboxamide with an acidic compound to obtain a 5-hydroxy-1H-imidazole-4-carboxamide acid salt or a hydrate thereof; and
reacting the resulting 5-hydroxy-1H-imidazole-4-carboxamide acid salt or hydrate thereof with a salt in the presence of an acidic solvent to obtain the 5-hydroxy-1H-imidazole-4-carboxamide.3/4 hydrate.

2 Claims, 16 Drawing Sheets

CRYSTAL OF 5-HYDROXY-1H-IMIDAZOLE-4-CARBOXAMIDE HYDRATE AND PHARMACEUTICAL COMPOSITION THEREOF

CROSS-REFERENCE TO RELATED APPLICATIONS

This application is a Divisional of copending application Ser. No. 14/226,364, filed on Mar. 26, 2014 which is a Continuation of International Application No. PCT/JP2012/075106, filed on Sep. 28, 2012, which claims priority under 35 U.S.C. §119(a) to Japanese Patent Application No. 2011-213501, filed in Japan on Sep. 28, 2011 and Japanese Patent Application No. 2011-213500, filed in Japan on Sep. 28, 2011, all of which are hereby expressly incorporated by reference into the present application.

TECHNICAL FIELD

The present invention relates to crystal of 5-hydroxy-1H-imidazole-4-carboxamide hydrate. In addition, the present invention relates to crystal of 5-hydroxy-1H-imidazole-4-carboxamide.3/4 hydrate and a method for producing the same.

BACKGROUND ART

5-Hydroxy-1H-imidazole-4-carboxamide (herein below, also referred to as "compound A") is a compound which is useful as a cancer inhibitor (see, Patent Document 1, for example).

The compound A is produced, for example, from 2-aminomalonamide (see, Non-Patent Document 1 and Patent Documents 1 and 2, for example).

It is disclosed in Non-Patent Document 1 that the compound A can be obtained by reacting 2-aminomalonamide with ethyl formimidate. However, because the production method has low yield, it is not completely satisfactory.

It is disclosed in Patent Document 1 that benzene sulfonate of the compound A can be obtained by reacting benzene sulfonate of 2-aminomalonamide with trimethyl orthoformate in the presence of benzene sulfonic acid. It is also disclosed that, by neutralizing the benzene sulfonate of the compound A with sodium hydrogen carbonate, it is possible to obtain the compound A.

However, this production method has disadvantages in that benzene sulfonic acid ester having genetic toxicity is generated and trimethyl orthoformate is required in a large amount. Therefore, it is difficult to say that the production method is indeed an industrially excellent production method. Further, the compound A obtained is colored and has poor storage stability. It is disclosed in Experimental Examples 1 and 2 of the Patent Document 1 that, even though the sulfonate of the compound A and the hydrochloric acid salt of the compound A are stable, color of the compound A itself is changed to navy or blue color. It is also disclosed in Patent Document 1 that, to obtain the compound A having excellent storage stability, a trace amount of acid needs to be included in the compound A. In Example 6, the compound A containing about 2.5% of benzoic acid is described. However, there is no concrete description regarding the stability.

It is disclosed in Patent Document 2 that crude crystal of the compound A can be obtained by reacting 2-aminomalonamide with triethyl orthoformate in the presence of sulfuric acid. However, this production method has disadvantageous in that a large amount of triethyl orthoformate is required and also a large amount of activated charcoal is required. Thus, it is difficult to say that the production method is indeed an industrially favorable production method. It is also described in Patent Document 2 that, by reacting crude crystal of the compound A with an acid and neutralizing it with ammonia, the compound A can be obtained. However, there is no concrete description regarding the stability.

For formulation production of the compound A, it is known that coloration with blue color can be prevented by containing an acidic material (see, Patent Document 3, for example). It is described in Patent Document 3 that "the present compound has a property of exhibiting color either by itself or caused by oxygen, heat, or light, and in a case in which the present compound is applied as an oral agent, for example, a tendency of showing more significant coloration based on more complex reaction pathways resulting from an interaction with co-existing excipients is observed."

PATENT DOCUMENT

Patent Document 1: International Publication No. 2009/035168
Patent Document 2: Japanese Patent Application Laid-Open (JP-A) No. 58-24569
Patent Document 3: JP-A No. 60-185727

NON-PATENT DOCUMENT

Non-Patent Document 1: Journal of American Chemical Society (J. Am. Chem. Soc.), vol. 74, pages 2892 to 2894, 1952.

SUMMARY OF INVENTION

Technical Problem

Until now, it is believed that the compound A has a problem in terms of storage stability due to coloration with blue color. It is also believed that, to obtain the compound A having excellent storage stability, the followings are required: (1) producing an acid salt of the compound A, (2) having co-presence of an acidic material, or (3) containing a trace amount of an acidic material. Further, the compound A having excellent storage stability without using additives in combination is hardly known until now. Meanwhile, the original compound used for medicines is strongly required to be a single compound with stability instead of a mixture.

An object of the invention is to provide crystal of the compound A which is excellent in storage stability. Another object of the invention is to provide crystal of the compound A having little impurities, having a small color difference between the crystal before storage and the crystal after storage, and excellent in storage stability, and a method for producing the same.

Solution to Problem

Under the circumstances, the inventors of the present invention conducted intensive studies, and as a result, found the following [1] to [24]. The invention was completed accordingly. Specific means for solving the problem is as follows.

[1] A method for producing a hydrate of the compound A including reacting 2-aminomalonamide with a compound represented by the following formula [1] in the presence of a carboxylic acid to obtain the compound A,

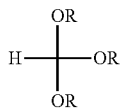

[1]

(in formula [1], each R independently represents a $C_{1-3}$ alkyl group), reacting the resulting compound A with an acidic compound to obtain an acid salt of the compound A or a hydrate thereof, and reacting the resulting acid salt of the compound A or the hydrate thereof with a salt in the presence of an acidic solvent to obtain a hydrate of the compound A.

[2] A method for producing a hydrate of the compound A including reacting 2-aminomalonamide with a compound represented by the following formula [1] in the absence of mineral acid and in the absence of sulfonic acid to obtain the compound A,

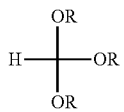

[1]

(in the formula, each R independently represents a $C_{1-3}$ alkyl group), reacting the resulting compound A with an acidic compound to obtain an acid salt of the compound A or a hydrate thereof, and reacting the resulting acid salt of the compound A or the hydrate thereof with a salt in the presence of an acidic solvent to obtain a hydrate of the compound A.

[3] The method for producing the hydrate of the compound A according to [2], wherein the obtaining of the compound A is performed in the presence of a carboxylic acid.

[4] The method for producing the hydrate of the compound A according to [1] or [3], wherein the carboxylic acid includes formic acid or oxalic acid.

[5] The method for producing the hydrate of the compound A according to any one of [1], [3], and [4], wherein the carboxylic acid is oxalic acid.

[6] The method for producing the hydrate of the compound A according to any one of [1], and [3] to [5], wherein a use amount of the carboxylic acid is from 0.001 molar times to 0.05 molar times that of the 2-aminomalonamide.

[7] The method for producing the hydrate of the compound A according to any one of [1] to [6], wherein the acidic compound is hydrochloric acid and the acid salt is hydrochloric acid salt.

[8] The method for producing the hydrate of the compound A according to any one of [1] to [7], wherein the acidic solvent is hydrochloric acid.

[9] The method for producing the hydrate of the compound A according to any one of [1] to [8], wherein the acidic solvent is from 0.3 mol/L to 0.8 mol/L hydrochloric acid.

[10] The method for producing the hydrate of the compound A according to any one of [1] to [9], wherein the salt is carboxylic acid salt.

[11] The method for producing the hydrate of the compound A according to any one of [1] to [10], wherein the salt is an alkali metal salt of carboxylic acid.

[12] The method for producing the hydrate of the compound A according to any one of [1] to [11], wherein the salt is an alkali metal salt of carboxylic acid that has a first acid dissociation constant (pKa1) of from 2 to 4.

[13] The method for producing the hydrate of the compound A according to any one of [1] to [12], wherein the salt is an alkali metal salt of carboxylic acid that has a first acid dissociation constant (pKa1) of from 3 to 4.

[14] A crystal of 5-hydroxy-1H-imidazole-4-carboxamide.3/4 hydrate (herein below, also referred to as the "hydrate of the compound A.") having an acidic compound content of 0.1% by mass or less, wherein, in a case in which the crystal is stored in conditions of a temperature of 40° C. and a relative humidity of 75% for 2 weeks, the crystal exhibits a color difference (ΔE) of 6 or less between before the storage and after the storage.

[15] The crystal of the hydrate of the compound A according to [14], wherein the color difference (ΔE) is 3 or less.

[16] The crystal of the hydrate of the compound A according to [14], wherein the color difference (ΔE) is 3 or less and the acidic compound content is 0.05% by mass or less.

[17] The crystal of the hydrate of the compound A according to any one of [14] to [16], wherein the crystal is colorless, pale yellow or yellow before the crystal is stored in conditions of a temperature of 40° C. and a relative humidity of 75% for 2 weeks.

[18] The crystal of the hydrate of the compound A according to any one of [14] to [16], wherein the crystal is colorless, or has a hue (H) in the Munsell color system of from 1Y to 6Y before the crystal is stored in conditions of a temperature of 40° C. and a relative humidity of 75% for 2 weeks.

[19] A hydrate of the compound A obtained by the production method according to any one of [1] to [13].

[20] A crystal of the hydrate of the compound A which is obtained by the production method according to any one of [1] to [13], and has an acidic compound content of 0.1% by mass or less, wherein, in a case in which the crystal is stored in conditions of a temperature of 40° C. and a relative humidity of 75% for 2 weeks, the crystal exhibits a color difference (ΔE) of 6 or less between before the storage and after the storage.

[21] The crystal of the hydrate of the compound A according to [20], wherein the color difference (ΔE) is 3 or less.

[22] The crystal of the hydrate of the compound A according to [20], wherein the color difference (ΔE) is 3 or less and the acidic compound content is 0.05% by mass or less.

[23] A crystal (hereinbelow, also referred to as "β type crystal") of a hydrate of the compound A, wherein the crystal has diffraction peaks at diffraction angles of 8.1, 12.6, 17.1, 19.3, 20.3 and 21.6°, represented by 2θ in a powder X-ray diffraction pattern.

[24] A pharmaceutical composition containing a crystal of a hydrate of the compound A, wherein the crystal has diffraction peaks at diffraction angles of 8.1, 12.6, 17.1, 19.3, 20.3 and 21.6°, represented by 2θ in a powder X-ray diffraction pattern.

Advantageous Effects of Invention

According to the present invention, crystal of the compound A having an excellent storage stability can be provided. According to the present invention, crystal of the compound A having little impurities, having a small color difference between the crystal before storage and the crystal after storage, and having an excellent storage stability and a method for producing the same can be further provided.

DESCRIPTION OF EMBODIMENTS

Figure 1:
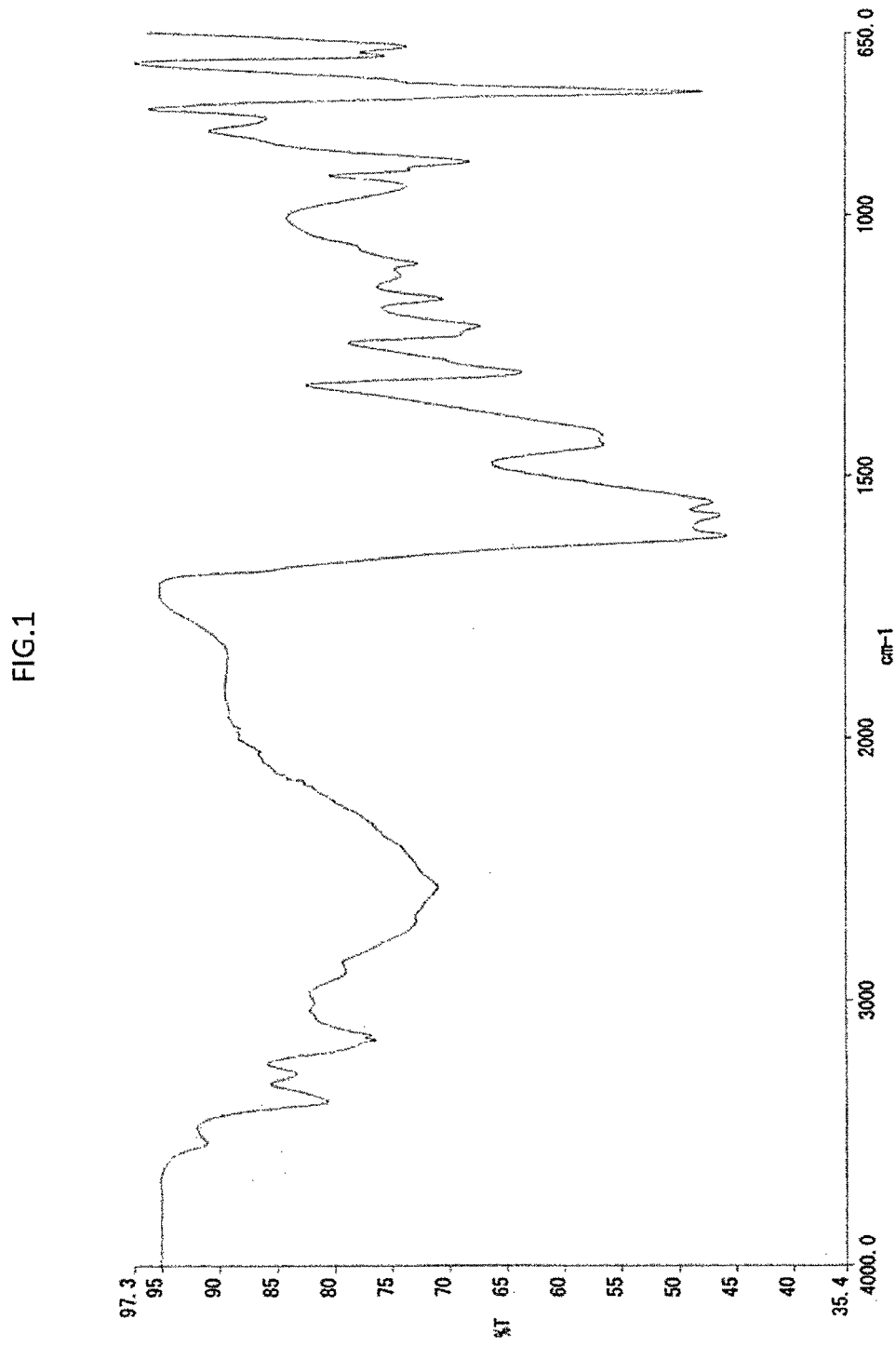
FIG. 1 is a drawing for illustrating one example of infrared absorption spectrum (ATR method) of the β type crystal.

The invention is explained in detail herein below. In the specification, the numerical ranges described as "A to B" indicate the range which includes each of the numerical values A and B as minimum value or maximum value. Further, as described herein, the amount of each component in the composition means the total amount of corresponding plural materials that are present in the composition in a case in which one or more materials corresponding to each component are present in the composition, unless specifically described otherwise.

Further, the terms as used herein are defined as follows, unless specifically described otherwise.

The $C_{1-3}$ alkyl group means a methyl group, an ethyl group, a propyl group, or an isopropyl group.

The halogenated hydrocarbons mean methylene chloride, chloroform, or dichloroethane.

The alcohols mean methanol, ethanol, propanol, 2-propanol, butanol, or 2-methyl-2-propanol.

The ethers mean diethyl ether, diisopropyl ether, dioxane, tetrahydrofuran, anisole, ethylene glycol dimethyl ether, diethylene glycol dimethyl ether, or diethylene glycol diethyl ether.

The ketones mean acetone, 2-butanone, or 4-methyl-2-pentanone.

The esters mean methyl acetate, ethyl acetate, propyl acetate, or butyl acetate.

The amides mean N,N-dimethyl formamide, N,N-dimethyl acetamide, or 1-methyl-2-pyrrolidone.

The alkali metal salts mean lithium salt, sodium salt, or potassium salt.

The Munsell color system is the color system developed by Albert H. Munsell. In the system, color is defined in terms of three attributions, hue, brightness and chroma. Hue (H) represents kinds of colors and, in the Munsell color system, hue is defined by using a total of 10 hues including 5 fundamental hues of red (R), yellow (Y), green (G), blue (B) and purple (P) and 5 intermediate hues of yellow-red (YR), yellow-green (YG), blue-green (BG), blue-purple (BP) and red-purple (RP). In addition, each hue of the 10 hues is further defined by using uniform color scales so that the maximum classification is 10. Hue (H) can be measured by using a measuring device such as a colorimeter or a color-difference meter.

Crystal of Hydrate of Compound a

First Embodiment

A crystal of the hydrate of the compound A of the present invention is characterized in that it has diffraction peaks at diffraction angles of 8.1, 12.6, 17.1, 19.3, 20.3 and 21.6°, represented by 2θ in a powder X-ray diffraction pattern.

Further, the crystal of the present invention has at least one of the following characteristics; (1) it does not contain additives, (2) it can be stored for a long period of time as there is no deterioration such as coloration even under a high temperature and high humidity conditions, (3) it has little impurities, (4) it has easy handlability, (5) it is produced by using a solvent safe for a human body, (6) it is produced under the conditions with low environmental burdens, and (7) it can be produced in large scale, and it is useful as an original drug substance of a pharmaceutical.

The aforementioned β type crystal has not been known until now, and it is a novel crystal which has never been described in the pamphlet of International Publication No. 2009/035168 or the like. Meanwhile, characteristic peaks by a powder X-ray diffraction may vary depending on conditions for measurement. In general, the error of 2θ occurs within the range of ±0.2°. Thus, the expression "diffraction angle of X° represented by 2θ" means the "diffraction angle of ((X−0.2) to (X+0.2)°) represented by 2θ."

X-ray diffraction can be measured based on Japanese Industry Standard JIS K 0131 or the like.

Figure 2:
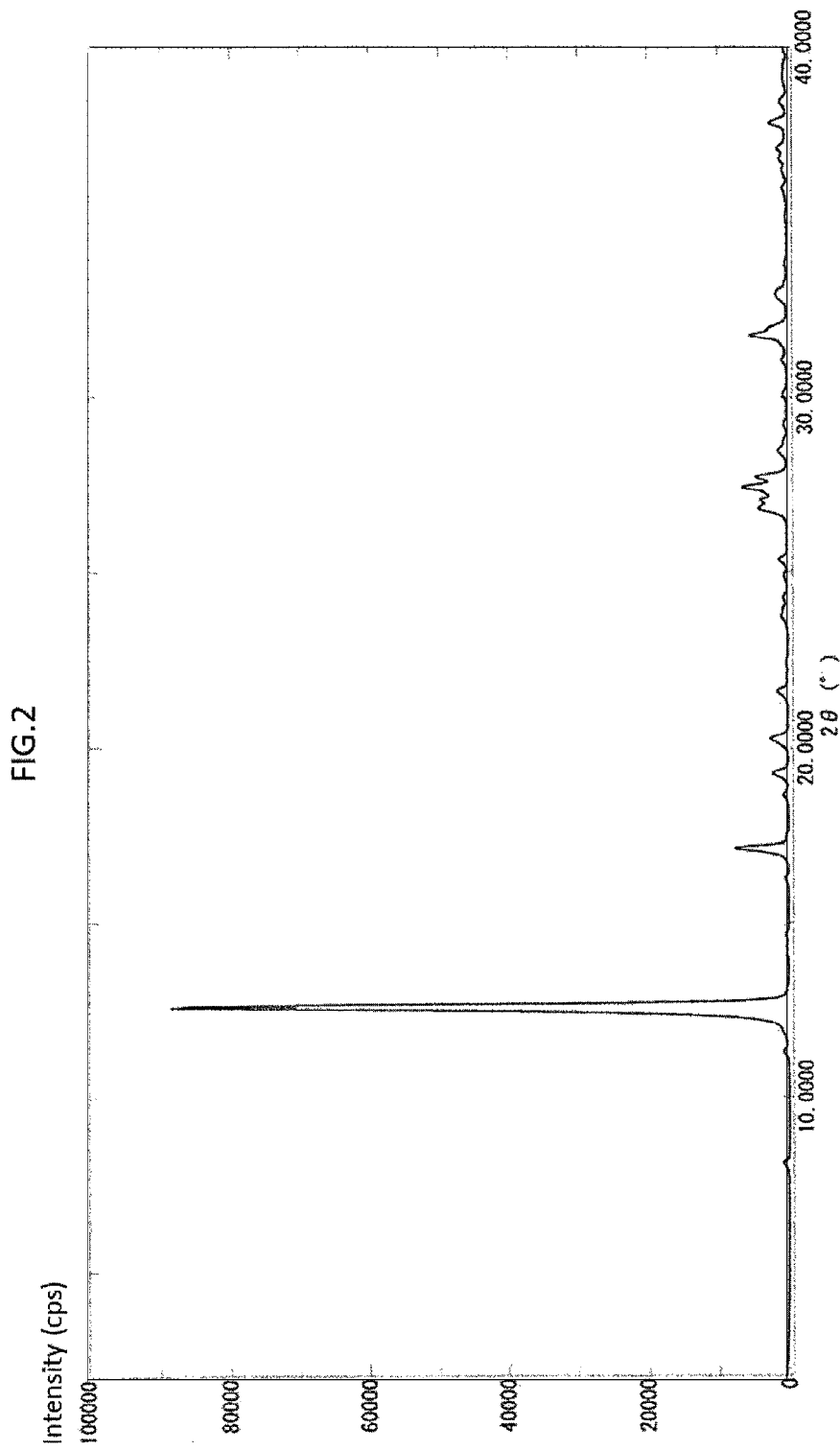
FIG. 2 is a drawing for illustrating one example of powder X ray diffraction pattern of the β type crystal.

One example of the measurement result of a powder X-ray diffraction for the β type crystal is illustrated in FIG. 2. Further, conditions for the measurement of a powder X-ray diffraction are described below.

(Conditions for measurement)
Anti-cathode: Cu
Tube voltage: 40 kV
Tube current: 40 mA
Scan axis: 2θ

Further, the β type crystal is also characterized by absorption wavelength in an infrared absorption spectrum measured under the following conditions.

One example of the result of infrared absorption spectrum measurement for the β type crystal is illustrated in FIG. 1. Meanwhile, the infrared absorption spectrum was measured according to Japanese Pharmacopoeia, general test methods, and infrared absorption spectrum—attenuated total reflectance method (ATR method).

As illustrated in FIG. 1, the β type crystal has characteristic peaks at 1614 cm-1, 1576 cm-1, and 1550 cm-1.

Next, the method for producing the β type crystal is explained. The β type crystal can be produced by the following method, for example.

[Production Method]

The β type crystal can be produced by heating and dissolving the compound A in an aqueous acid solution followed by slow cooling for crystallization. Here, the compound A can be produced by the method described in the pamphlet of International Publication No. 2009/035168, for example.

Examples of the acid include an organic acid such as acetic acid and oxalic acid and an inorganic acid such as hydrochloric acid. It may be used either singly or in combination of two or more types. Preferred examples of the acid include an organic acid such as acetic acid and oxalic acid. Acetic acid is more preferable.

An acid concentration in an aqueous acid solution is not particularly limited, and it can be suitably selected depending on a type of the acid to be used. The acid concentration is preferably 1% by mass to 10% by mass, and more preferably 3% by mass to 7% by mass, for example.

The temperature for heating and dissolving the compound A in an aqueous acid solution is not particularly limited, and it can be suitably selected depending on a type or an amount of the aqueous acid solution. For example, it can be 50° C. to 100° C. It is preferably 75° C. to 100° C., and more preferably 80° C. to 98° C.

The crystallization temperature is not particularly limited. It is preferably 50° C. to 100° C., more preferably 50° C. to 80° C., and still more preferably 60° C. to 80° C.

A use amount of the aqueous acid solution for dissolving the compound A is not particularly limited. For examples, it is preferably 10 times (v/w) to 50 times, and more preferably 15 times (v/w) to 40 times that of the compound A.

For the aforementioned production method, a salt is preferably present during crystallization. By performing slow cooling in the presence of a salt, a crystal with more excellent stability can be obtained efficiently.

Examples of the salt that is used as desired include an alkali metal salt of a carboxylic acid. Specifically, at least one selected from sodium acetate, potassium acetate, sodium formate, potassium formate, sodium benzoate, sodium citrate, sodium malate, sodium fumarate, and sodium succinate is preferable. At least one selected from sodium formate, sodium acetate, sodium citrate, sodium malate, sodium fumarate, and sodium succinate is more preferable. At least one selected from sodium formate and sodium acetate is still more preferable.

The time required for crystallization in the aforementioned production method is not particularly limited. For examples, it is preferably 0.5 hour to 48 hours, and more preferably 0.5 hour to 6 hours.

Further, it is preferable to use seed crystal for crystallizing the β type crystal. Accordingly, the crystal type can be more homogeneously controlled.

Meanwhile, as for the seed crystal, those obtained by previous production can be used, or part of the crystallized seeds may be filtered and collected in advance, and used as seed crystal.

Temperature for filtering and collecting the crystallized β type crystal is, although not particularly limited, preferably the same as the crystallization temperature.

Further, although atmosphere for crystallization is not particularly limited, it is preferably performed under inert gas atmosphere. Examples of the inert gas atmosphere include argon atmosphere and nitrogen atmosphere.

<Pharmaceutical Composition>

The pharmaceutical composition of the present invention contains the β type crystal, and it is constituted by containing other components, if necessary. By containing the β type crystal, the pharmaceutical composition has excellent storage stability.

In a case in which the β type hydrate is used as a pharmaceutical composition, a formulation aid that is generally used for formulation, for example, an excipient, a carrier, or a diluents, may be appropriately mixed. It may be administered according to a common method either orally or parenterally in the form of a tablet, a capsule, powder, syrup, a granule, a pill, a suspension, an emulsion, a liquid, a powder formulation, a suppository, an eye dropping formulation, a nasal formulation, an ear drop, a patch, an ointment, or an injection solution. Further, a method for administration, dosage, and number of administration can be appropriately selected depending on age, body weight, and symptoms of a subject to be treated. In general, for an adult, 0.01 mg/kg to 1000 mg/kg may be administered per day either once or divided in several portions according to oral or parenteral administration (for example, injection, liquid drop, or rectal administration).

Usefulness of the invention is explained in view of Examples given below.

<Crystal of Hydrate of Compound A—Second Aspect—>

A crystal of the hydrate of the compound A according to the present invention has a color difference (ΔE) between the crystal before storage and the crystal after storage for 2 weeks in conditions of a temperature of 40° C. and a relative humidity of 75% of 6 or less, and the crystal has an acidic compound content of 0.1% by mass or less.

The crystal of hydrate of the compound A has a color difference (ΔE) between the crystal before storage and the crystal after storage for 2 weeks in conditions of a temperature of 40° C. and a relative humidity of 75% of 6 or less. However, from the viewpoint of storage stability, it is preferably 3 or less. As described herein, the color difference of the crystal is measured by reflection method using a spectrocolorimeter.

The crystal of the hydrate of the compound A is preferably colorless, pale yellow or yellow, more preferably colorless or pale yellow before the crystal is stored in conditions of a temperature of 40° C. and a relative humidity of 75% for 2 weeks.

The crystal of the hydrate of the compound A preferably has a hue (H) in the Munsell color system of from 1Y to 6Y before the crystal is stored in conditions of a temperature of 40° C. and a relative humidity of 75% for 2 weeks.

Further, the acidic compound content contained in the crystal of the hydrate of the compound A is preferably 0.1% by mass or less. However, from the viewpoint of storage stability, it is more preferably 0.05% by mass or less. Further, the acidic compound content contained in the crystal of the hydrate of the compound A is measured by a common analytical method that is suitably selected depending on the type of the acidic compound. For example, the acidic compound content contained in the crystal of the hydrate of the compound A can be measured by high performance liquid chromatography (HPLC), ion chromatography, or gas chromatography. For example, the acidic compound content contained in the crystal of the hydrate produced in Example 9 was measured by ion chromatography. The measurement result shows that the acidic compound content was 0.05% by mass or less (below the limit of determination).

Examples of the acidic compound contained in the crystal of the hydrate of the compound A include a mineral acid, a sulfonic acid, or a carboxylic acid which are described below. In a case in which the acidic compound is contained in the crystal of the hydrate of the compound A, a sulfonic acid or a carboxylic acid is preferable.

<Method for Producing Hydrate of the Compound A>

The first production method of the present invention includes steps of reacting 2-aminomalonamide with a compound represented by the following formula [1] in the presence of a carboxylic acid to obtain the compound A,

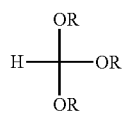

[1]

(in the formula, each R independently representing a $C_{1-3}$ alkyl group), reacting the resulting compound A with an acidic compound to obtain an acid salt or a hydrate of the acid salt, and reacting the resulting acid salt or the resulting hydrate of the acid salt with a salt in the presence of an acidic solvent to obtain a hydrate of the compound A, and if necessary, other steps.

Further, the second production method of the present invention includes steps of reacting 2-aminomalonamide with a compound represented by the following formula [1] in the absence of mineral acid and in the absence of sulfonic acid to obtain the compound A,

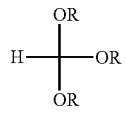

[1]

(in the formula, each R independently representing a $C_{1-3}$ alkyl group), reacting the resulting compound A with an acidic compound to obtain an acid salt or a hydrate of the acid salt, and reacting the resulting acid salt or the resulting hydrate of the acid salt with a salt in the presence of an acidic solvent to obtain a hydrate of the compound A, and if necessary, other steps.

The hydrate of the compound A that is obtained by the production method according to the present invention has characteristics that (1) it does not contain additives, (2) a color difference between the crystal before storage and the crystal after storage is small, (3) it is excellent in storage stability, and (4) it has little impurities. Further, as it is unnecessary to contain a trace amount of acid for improving stability, the hydrate of the compound A is highly pure. Further, as it is unnecessary to control the content of acid at constant level, it is possible to produce with excellent productivity a large amount of the hydrate of the compound A.

The method for producing hydrate of the compound A according to the present invention also has characteristics that (5) a benzene sulfonic acid ester having genetic toxicity is not generated, and that (6) large excess of orthoformic acid triester is not required.

Thus, the production method of the present invention is useful as a method for industrial production of a hydrate of the compound A.

Further, according to another embodiment of the present invention, the method for producing hydrate of the compound A is characterized in that it can be controlled to uniform crystal form at even lower temperature.

According to the production method of the present invention, it becomes possible for the first time to produce a hydrate of the compound A in which (1) it does not contain additives, (2) a color difference between the crystal before storage and the crystal after storage is small, (3) it is excellent in storage stability, and (4) it has little impurities.

Thus, the production method of the present invention is useful as a method for industrial production of the hydrate of the compound A.

The hydrate of the compound A obtained by the method of the present invention is preferably colorless, pale yellow or yellow, and more preferably colorless or pale yellow.

The hydrate of the compound A obtained by the method of the present invention preferably has a hue (H) in the Munsell color system of from 1Y to 6Y.

(First Step)

The compound A can be produced by a method (A) including reacting 2-aminomalonamide with a compound represented by formula [1] in the presence of a carboxylic acid or by a method (B) including reacting 2-aminomalonamide with a compound represented by formula [1] in the absence of mineral acid and in the absence of sulfonic acid. In the formula, R has the same definition as described above.

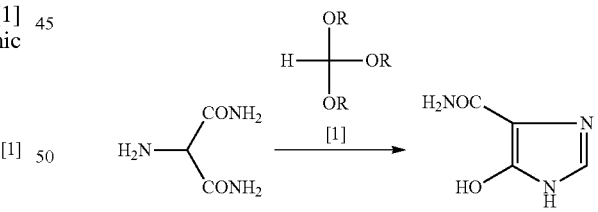

Examples of the compound represented by formula [1] include trimethyl orthoformate and triethyl orthoformate.

A commercially available compound represented by formula [1] may contain a basic compound such as triazine as impurity. For such case, it is preferable to carry out the reaction in the presence of a carboxylic acid.

In a case in which the compound represented by formula [1] does not contain a basic compound such as triazine, the reaction can be performed without using a carboxylic acid.

The reaction is preferably carried out in the presence of a solvent. The solvent that may be used is not specifically limited as long as it is generally used as a solvent. Examples thereof include halogenated hydrocarbons; alcohols; ethers; ketones; esters; amides; acetonitrile and dimethyl sulfoxide.

It may be used either singly or in combination of two or more. Further, the compound represented by formula [1] may be used as a solvent.

Preferred examples of the solvent include alcohols. Ethanol and 2-propanol are more preferable. 2-Propanol is still more preferable.

A use amount of the solvent is not specifically limited. Preferably, it is an amount of 1 to 100 times (v/w) the 2-aminomalonamide. More preferably, it is an amount of 10 to 30 times (v/w). Still more preferably, it is an amount of 15 to 25 times (v/w).

For the first step, it is preferable to use a compound in which R representing a methyl group or an ethyl group. It is more preferable to use a compound in which R representing an ethyl group.

A use amount of the compound represented by formula [1] is preferably an amount of 1 to 10 molar times that of the 2-aminomalonamide. More preferably, it is an amount of 1 to 5 molar times thereof. Still more preferably, it is an amount of 2 to 3 molar times thereof Examples of the mineral acid include hydrochloric acid, nitric acid, phosphoric acid, and sulfuric acid. Further, examples of the sulfonic acid include an organic sulfonic acid such as methane sulfonic acid, ethane sulfonic acid, benzene sulfonic acid, and toluene sulfonic acid.

Examples of the carboxylic acid include aliphatic carboxylic acids such as formic acid and acetic acid; hydroxyl acids such as lactic acid, malic acid, citric acid, and tartaric acid; aromatic carboxylic acids such as benzoic acid and phthalic acid; and dicarboxylic acids such as oxalic acid, fumaric acid, and maleic acid. Formic acid or oxalic acid is preferable. Oxalic acid is more preferable.

A use amount of the carboxylic acid is preferably an amount of from 0.001 to 0.05 molar times that of the 2-aminomalonamide. More preferably, it is an amount of from 0.001 to 0.01 molar times thereof. Still more preferably, it is an amount of from 0.002 to 0.01 molar times thereof.

The reaction temperature is preferably 0° C. to 150° C., more preferably 70° C. to 100° C., and still more preferably 75° C. to 85° C.

The reaction time is preferably from 5 hours to 50 hours. More preferably, it is from 5 hours to 10 hours.

Further, the reaction atmosphere is not specifically limited, but the reaction is preferably carried out under inert gas atmosphere. Examples of the inert gas atmosphere include argon atmosphere and nitrogen atmosphere.

The compound A obtained from the first step may be used for the next step after isolation. However, it is preferable to use it for the next step without any isolation.

In a case in which there are a solvate, a hydrate, and crystal of various forms present for the compound A obtained from the first step, they are also included in the invention.

A method for producing the compound A has been already known. For example, it is disclosed in JP-A No. 58-24569 that crude crystal of the compound A can be obtained by reacting 2-aminomalonamide with triethyl orthoformate in the presence of sulfuric acid.

The inventors of the present invention tried to produce the compound A with reference to the production method described in JP-A No. 58-24569. However, the reaction liquid was colored with deep blue color. The reaction was also performed by using p-toluene sulfonic acid instead of sulfuric acid. However, the reaction liquid was also colored with deep blue color.

On the other hand, according to the method for producing the compound A according to the first step, coloration of the reaction liquid was inhibited.

(Second step)

By reacting the compound A obtained from the first step with an acidic compound, an acid salt or a hydrate of the acid salt can be produced.

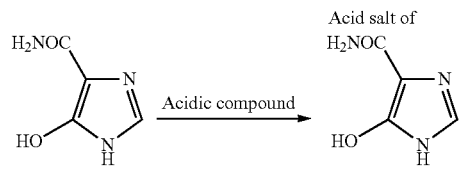 [SMILES: NC(=O)c1nc[nH]c1O ; NC(=O)c1nc[nH]c1O]

The method for reacting the compound A with an acidic compound is not specifically limited, and it can be appropriately selected from commonly practiced methods. Specifically, by adding an aqueous solution containing an acidic compound to a solution or a suspension containing the compound A, the compound A can be reacted with the acidic compound.

The acidic compound is not specifically limited. Examples thereof include a mineral acid such as hydrochloric acid and sulfuric acid; an organic sulfonic acid such as methane sulfonic acid, ethane sulfonic acid, benzene sulfonic acid, and toluene sulfonic acid; and oxalic acid. Mineral acid is preferable. Hydrochloric acid is more preferable.

Examples of the acid salt include a salt with a mineral acid such as hydrochloric acid and sulfuric acid; a salt with organic sulfonic acids such as methane sulfonic acid, ethane sulfonic acid, benzene sulfonic acid, and toluene sulfonic acid; and a salt with oxalic acid. Salt with a mineral acid are preferable. Hydrochloric acid salt is more preferable.

The reaction temperature and reaction time for the second step are not specifically limited, and they can be suitably selected depending on the type of an acidic compound used.

Further, the reaction atmosphere is not specifically limited, but the reaction is preferably carried out under inert gas atmosphere. Examples of the inert gas atmosphere include argon atmosphere and nitrogen atmosphere.

The acid salt of the compound A obtained from the second step may be used for the next step without isolation. However, it is preferable to use for the next step after any isolation.

In a case in which there are a solvate, a hydrate, and crystal of various forms present for the acid salt of the compound A obtained from the second step, they are also included in the invention.

(Third Step)

By reacting the acid salt or the hydrate of the acid salt obtained from the second step with a salt in the presence of an acidic solvent, a hydrate of the compound A can be produced.

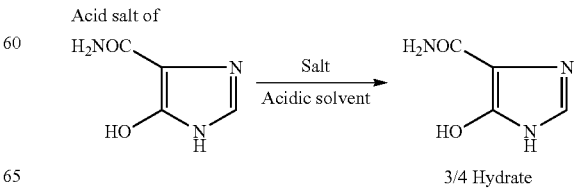

Examples of the acidic solvent include an aqueous solution of a mineral acid. Specific examples thereof include hydrochloric acid, sulfuric acid, and nitric acid. Hydrochloric acid is preferable. By using hydrochloric acid, uniform crystal of the hydrate of the compound A can be produced at even lower temperature condition.

A use amount of the acidic solvent is not specifically limited. It may be 5 to 50 times (v/w) the acid salt of the compound A.

Concentration of the acidic solvent is not specifically limited. In a case in which hydrochloric acid is used, for example, concentration of hydrochloric acid is preferably 0.3 mol/L to 0.8 mol/L, and more preferably 0.4 mol/L to 0.5 mol/L.

As a salt, an organic acid salt is preferably used. Examples of the organic acid salt include a salt of carboxylic acid. An alkali metal salt of the carboxylic acid is preferable. An alkali metal salt of the carboxylic acid having a first acid dissociation constant (pKa1) of from 2 to 4 is preferable. An alkali metal salt of the carboxylic acid having a first acid dissociation constant (pKa1) of from 3 to 4 is more preferable.

Examples of the alkali metal salt of the carboxylic acid include sodium acetate, potassium acetate, lithium formate, sodium formate, potassium formate, sodium benzoate, sodium citrate, sodium malate, sodium fumarate, and sodium succinate. At least one selected from sodium formate, potassium formate, sodium citrate, sodium malate, or sodium fumarate is preferable. At least one selected from sodium formate, sodium malate, or sodium citrate is more preferable. Sodium formate is still more preferable.

Examples of the alkali metal salt of the carboxylic acid having a first acid dissociation constant (pKa1) of from 2 to 4 include sodium malate, sodium tartarate, potassium tartarate, potassium hydrogen tartarate, sodium hydrogen tartarate, lithium formate, sodium formate, potassium formate, sodium citrate, sodium malate, and sodium fumarate.

Examples of the alkali metal salt of the carboxylic acid having a first acid dissociation constant (pKa1) of from 3 to 4 include lithium formate, sodium formate, potassium formate, sodium citrate, sodium malate, and sodium fumarate. At least one selected from sodium formate, sodium malate, or sodium citrate is preferable. Sodium formate is more preferable.

A use amount of the salt can be suitably selected depending on type of the acid salt, type of the salt, and type and concentration of the acidic solvent. For example, the use amount of the salt is preferably controlled such that pH of a suspension or solution of the compound A after adding the salt is 1 to 4. It is more preferable that the use amount of the salt is controlled such that pH of a suspension or solution is 1.5 to 2.5.

Specifically, in a case in which the hydrochloric acid salt of the compound A is dissolved in 0.4 mol/L to 0.5 mol/L hydrochloric acid and reacted with sodium formate, the preferred use amount of sodium formate is from 1.8 molar times to 3.0 molar times that of the hydrochloric acid salt of the compound A.

The third step can be performed by adding a salt to a suspension or a solution of an acid salt of the compound A. A method of adding a salt to a solution of an acid salt of the compound A is preferable.

Specifically, it is possible that an acid salt of the compound A is added to an acidic solvent followed by, if necessary, heating to prepare a solution of acid salt of the compound A and a salt is added to the solution.

The acid and base which constitute the salt to be used in the third step may be added in a manner in which each of the acid and the base is added, separately, in this order to a suspension or a solution of an acid salt of the compound A.

For example, instead of using sodium formate as a salt, after adding formic acid to a suspension or a solution of an acid salt of the compound A, sodium hydroxide or the like may be added thereto.

The reaction temperature for the third step is preferably from room temperature to 60° C., and more preferably 40° C. to 50° C.

The reaction time may be from 1 minute to 24 hours, for example.

Further, the reaction atmosphere is not specifically limited, but the reaction is preferably carried out under inert gas atmosphere. Examples of the inert gas atmosphere include argon atmosphere and nitrogen atmosphere.

Method for producing a hydrate of the compound A has been already known. For example, in the pamphlet of International publication No. 2009/035168, it is disclosed that a hydrate of the compound A can be produced by reacting benzene sulfonate of the compound A with sodium hydrogen carbonate. Further, in JP-A No. 58-24569, a method of using ammonia water is disclosed.

The inventors of the present invention tried to produce the hydrate of the compound A according to the methods described above. However, the hydrate of the compound A obtained was colored with blue color when the addition amount of sodium hydrogen carbonate or ammonia water is just above the equivalent point. On the other hand, the hydrate of the compound A that is obtained by using a salt of carboxylic acid is not colored even when the addition amount is well over the equivalent point.

In a case in which the hydrate of the compound A obtained by the production method according to the present invention is used as a pharmaceutical preparation, a formulation aid that is generally used for formulation, for example, an excipient, a carrier, or a diluents, may be appropriately mixed. It may be administered according to a common method either orally or parenterally in the form of a tablet, a capsule, powder, syrup, a granule, a pill, a suspension, an emulsion, a liquid, a powder formulation, a suppository, an eye dropping formulation, a nasal formulation, an ear drop, a patch, an ointment, or an injection solution. Further, a method for administration, dosage, and number of administration can be appropriately selected depending on age, body weight, and symptoms of a subject to be treated. In general, for an adult, 0.01 mg/kg to 1000 mg/kg may be administered per day either once or divided in several portions according to oral or parenteral administration (for example, injection, liquid drop, or rectal administration).

Usefulness of the invention is explained in view of Examples given below.

EXAMPLES

Herein below, the present invention is explained in view of Reference Examples, Examples and Comparative Examples. However, it is evident that the invention is not limited to them. Further, unless specifically described otherwise, "%" means "% by mass."

Hereinbelow, examples relating to the crystal of 5-hydroxy-1H-imidazole-4-carboxamide hydrate of the present invention will be described.

Example 1

Under the nitrogen atmosphere, 5.0 g of 5-hydroxy-1H-imidazole-4-carboxamide was added with 150 ml of 5% aqueous solution of acetic acid and dissolved therein by heating at 82° C. followed by slow cooling. After confirming precipitation of the crystal at 50° C., it was heated at internal temperature of 75° C. and stirred at the same temperature for 15 minutes. The solution was slowly cooled. The crystal precipitated at 50° C. was collected by filtration followed by washing three times with 10 ml of acetone and air drying, and thus 1.7 g of the type crystal was obtained.

The infrared absorption spectrum (ATR method) of the obtained β type crystal is illustrated in FIG. 1.

IR (ATR) 1614 cm-1, 1576 cm-1, 1550 cm-1

Further, the powder X-ray diffraction pattern of the obtained β type crystal is the same as Example 2 described below.

Example 2

Under the nitrogen atmosphere, 10.0 g of 5-hydroxy-1H-imidazole-4-carboxamide and 7.04 g of oxalic acid were added with 200 ml of water and dissolved therein by heating at 95° C. To the mixture, 5.54 g of sodium acetate was added, cooled slowly, and at 85° C., 0.1 g of the crystal obtained in Example 1 was added. Stirring was performed at 65° C. for 40 minutes, and the crystal precipitated at the same temperature was collected by filtration. According to washing with 30 ml of 5% aqueous acetic acid solution followed by washing two times with 30 ml of acetone and air drying, 4.65 g of the β type crystal was obtained.

The powder X-ray diffraction pattern of the obtained β type crystal is illustrated in FIG. 2 and Table 1.

Further, the infrared absorption spectrum (ATR method) is the same as Example 1.

TABLE 1

| 2θ (°) | d Value (Å) | Relative intensity (%) |
|---|---|---|
| 8.1 | 10.9 | 1 |
| 12.6 | 7.0 | 100 |
| 17.1 | 5.2 | 10 |
| 19.3 | 4.6 | 3 |
| 20.3 | 4.4 | 4 |
| 21.6 | 4.1 | 2 |

Example 3

Under the nitrogen atmosphere, 5.0 g of 5-hydroxy-1H-imidazole-4-carboxamide was added with 150 mL of 5% aqueous solution of acetic acid and dissolved therein by heating at 85° C. It was then cooled slowly until the crystal starts to precipitate. After precipitation of the crystal, the solution was heated to 83° C. and then cooled again to have solution temperature of 50° C. The precipitated crystal was collected by filtration and then washed three times with 5 mL of acetone followed by air drying to obtain 2.3 g of the β type crystal.

The powder X-ray diffraction pattern of the obtained β type crystal is the same as Example 2 and the infrared absorption spectrum (ATR method) is the same as Example 1.

Comparative Example 1

With reference to the method described in Example 6 of the pamphlet of International Publication No. 2009/035168, 5-hydroxy-1H-imidazole-4-carboxamide was obtained as pale yellow powder.

As a result of the analysis by high performance liquid chromatography, the obtained 5-hydroxy-1H-imidazole-4-carboxamide contains benzoic acid in an amount of about 0.15%.

Figure 3:
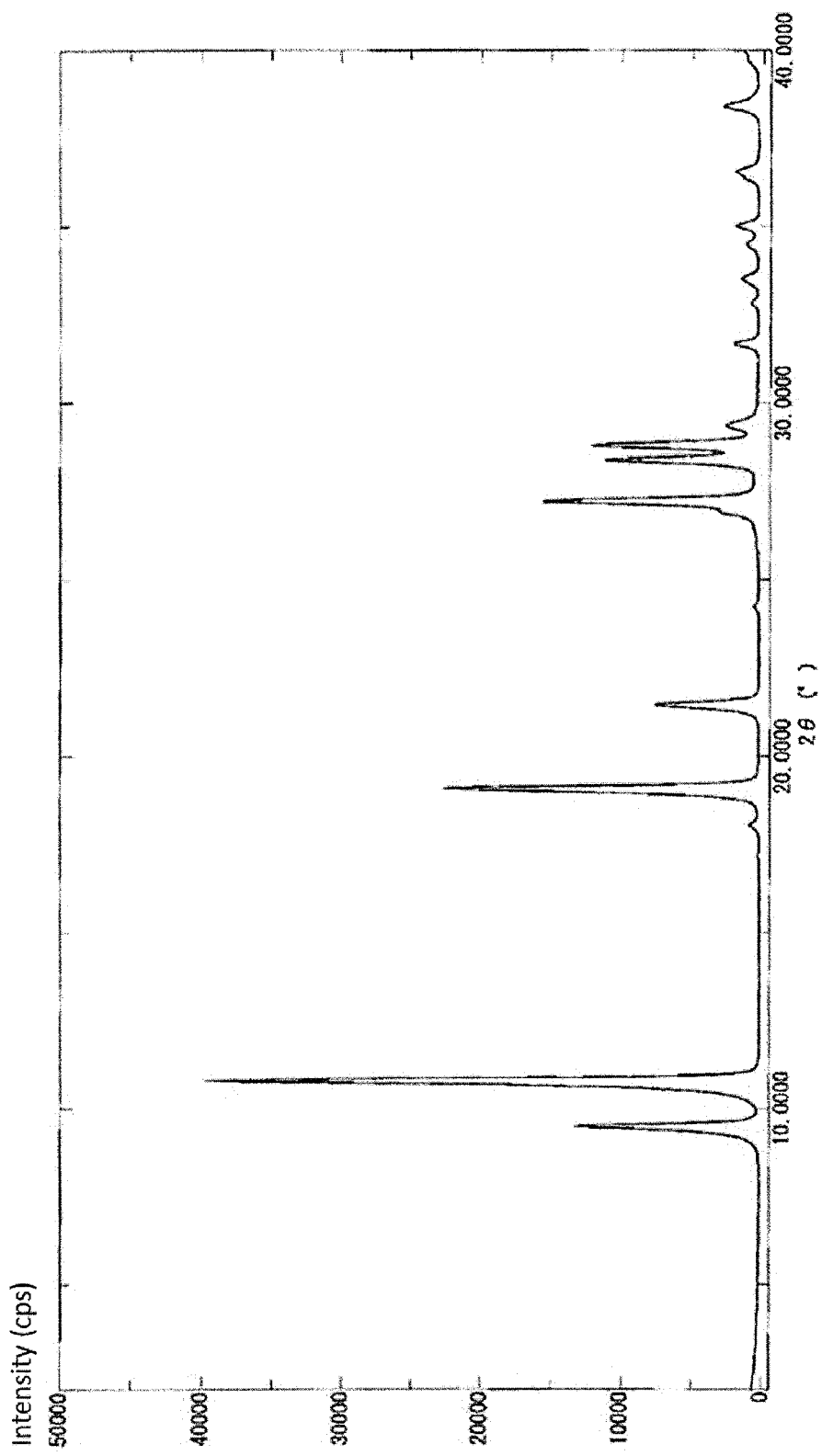
FIG. 3 is a drawing for illustrating one example of powder X ray diffraction pattern of the crystal of the compound A which has been obtained in Comparative Example 1.

The powder X-ray diffraction pattern is illustrated in FIG. 3 and Table 2.

TABLE 2

| 2θ (°) | d Value (Å) | Relative intensity (%) |
|---|---|---|
| 9.5 | 9.3 | 33 |
| 10.8 | 8.2 | 100 |
| 19.1 | 4.7 | 60 |
| 21.4 | 4.1 | 20 |
| 27.2 | 3.3 | 43 |
| 28.4 | 3.1 | 30 |
| 28.8 | 3.1 | 32 |

Test Example 1

Storage stability test under high temperature and high humidity conditions

As a test material, the crystals obtained from Example 3 and Comparative Example 1 were selected.

Each of the test material (about 0.2 g) was added to a glass vial and stored for one week under the conditions including temperature of 60° C. and relative humidity of 75%.

Figure 4:
FIG. 4 is a photographic image illustrating one example of the β type crystal.
Figure 5:
FIG. 5 is a photographic image illustrating the state of the β type crystal after storage for one week in conditions of a temperature of 60° C. and relative humidity of 75%.
Figure 6:
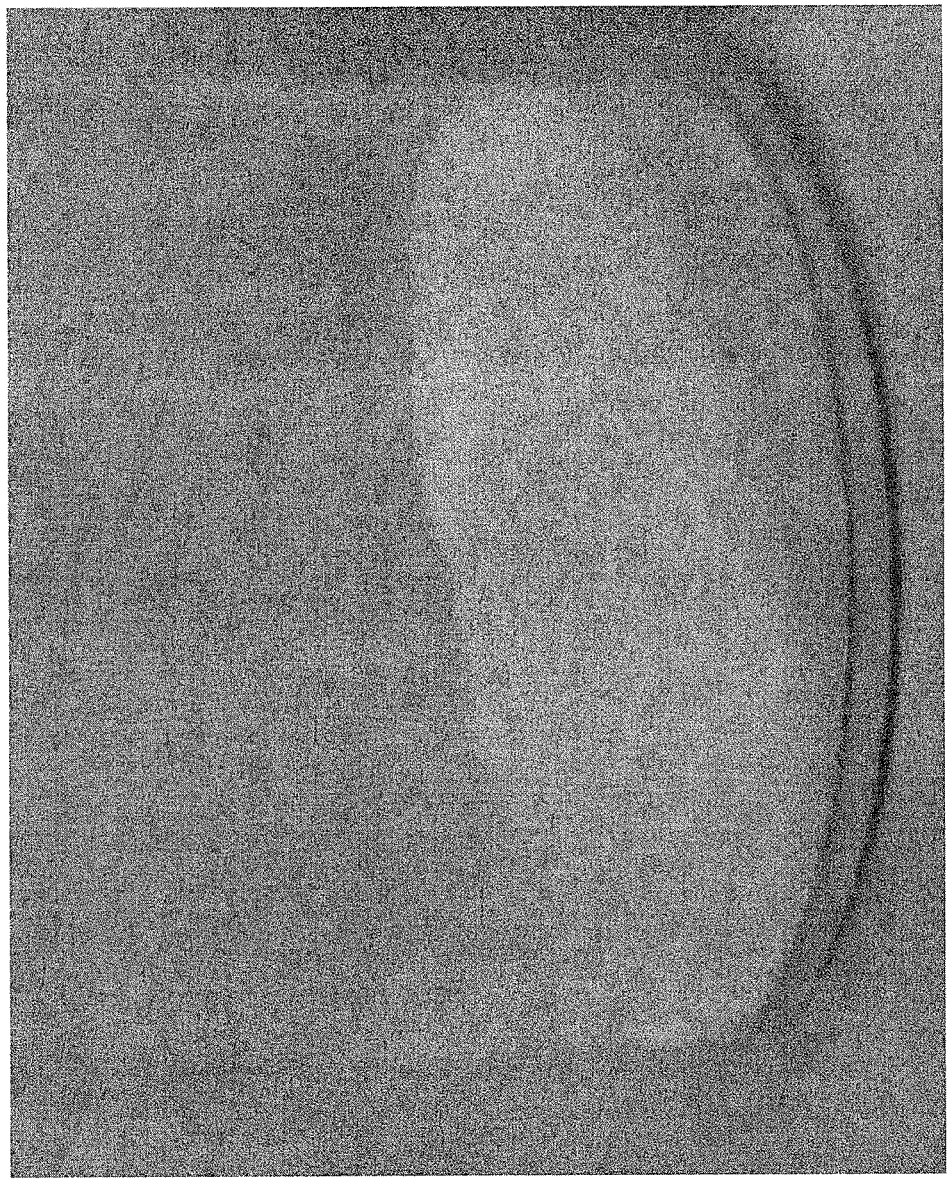
FIG. 6 is a photographic image illustrating one example of the crystal of the compound A which has been obtained in Comparative Example 1.
Figure 7:
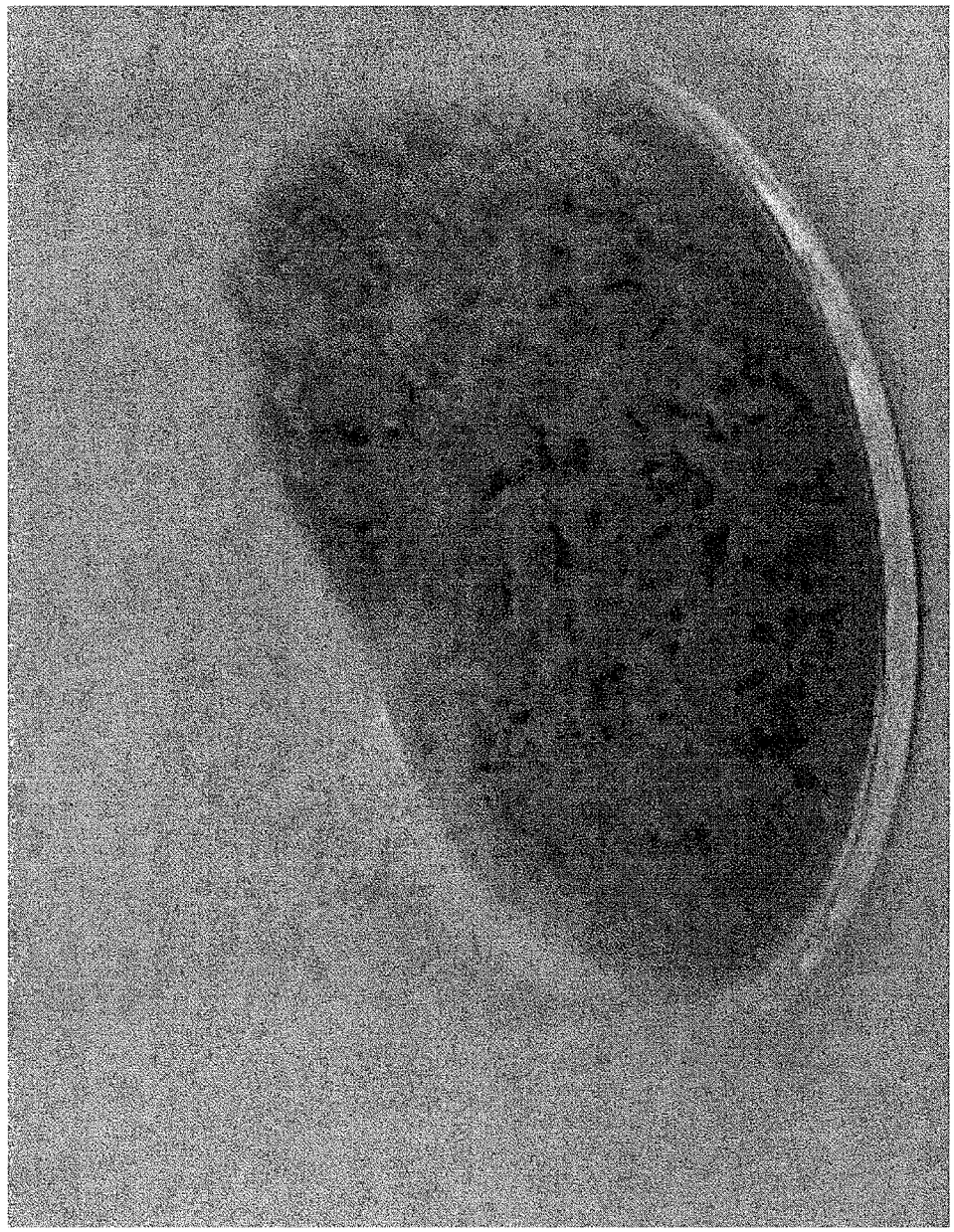
FIG. 7 is a photographic image illustrating the state of the crystal of 5-hydroxy-1H-imidazole-4-carboxamide after storage for one week in conditions of a temperature of 60° C. and relative humidity of 75%.

State of the crystal of Example 3 before starting the test is illustrated in FIG. 4 and state of the crystal of Example 3 after finishing the test is illustrated in FIG. 5. Further, state of the crystal of Comparative Example 1 before starting the test is illustrated in FIG. 6 and state of the crystal of Comparative Example 1 after finishing the test is illustrated in FIG. 7.

It was found that the β type crystal obtained from Example 3 has clearly less coloration and better storage stability when compared to the compound of Comparative Example 1.

Hereinbelow, Examples relating to production of 5-hydroxy-1H-imidazole-4-carboxamide.3/4 hydrate of the present invention will be described.

Condition for measurement of powder X-ray diffraction
Anti-cathode: Cu
Tube voltage: 40 kV
Tube current: 40 mA
Scan axis: 2θ

Further, the characteristic peaks in powder X-ray diffraction may vary depending on measurement condition. In general, the error of 2θ occurs within the range of ±0.2°. Thus, the expression "diffraction angle of X° represented by 2θ" means the "diffraction angle of ((X−0.2) to (X+0.2)°) represented by 2θ."

Following reagents were used.

2-Aminomalonamide: Tateyama Kasei (Lot No. 091026)

Triethyl orthoformate: NIPPOH CHEMICALS CO., LTD. (Lot No. OJ1401, purity: 99.5%, containing a basic compound such as triazine as impurity) (Reference Examples 1, 2, and 4, Examples 9 and 10, and Comparative Examples 2, 3, 6, and 7)

Triethyl orthoformate: Wako Pure Chemical Industries, Ltd. (Lot No. CDM1714) (Reference Example 3 and Example 11)

Reference Example 1

Under the nitrogen atmosphere, 10 g of 2-aminomalonamide and 19.7 mg of formic acid were added to 200 mL of 2-propanol. After heating to 80° C., 35.4 mL of triethyl orthoformate was added dropwise to the mixture over 5 minutes. Subsequently, the reaction mixture was stirred for 8 hours at 80° C. Color of the reaction liquid was pale blue when the reaction was completed. Subsequently, after cooling to 56° C., the reaction mixture was added with 10 mL of water followed by 8 mL of conc. hydrochloric acid. After cooling with water, the crystal was collected by filtration and then washed with 40 mL of acetone to give 16 g of 5-hydroxy-1H-imidazole-4-carboxamide hydrochloric acid salt dihydrate as a pale yellowish green crystal.

Reference Example 2

Under the nitrogen atmosphere, 10 g of 2-aminomalonamide and 38.4 mg of oxalic acid were added to 200 mL of 2-propanol. After heating to 80° C., 35.4 mL of triethyl orthoformate was added dropwise to the mixture over 5 minutes. Subsequently, the reaction mixture was stirred for 8 hours at 80° C. Color of the reaction liquid was pale yellow when the reaction was completed. Subsequently, after cooling to 53° C., the reaction mixture was added with 10 mL of water followed by 8 mL of conc. hydrochloric acid. After cooling with water, the crystal was collected by filtration and then washed with 40 mL of acetone to give 16 g of 5-hydroxy-1H-imidazole-4-carboxamide hydrochloric acid salt dihydrate as a pale yellow crystal.

Reference Example 3

Under the nitrogen atmosphere, 10 g of 2-aminomalonamide and 35.4 mL of triethyl orthoformate were added to 200 mL of 2-propanol. After heating to 80° C., the reaction mixture was stirred for 8 hours at the same temperature. Color of the reaction liquid was pale yellow when the reaction was completed. Subsequently, after cooling to 57° C., the reaction mixture was added with 10 mL of water followed by 8 mL of conc. hydrochloric acid. After cooling with water, the crystal was collected by filtration and then washed with 40 mL of acetone to give 16 g of 5-hydroxy-1H-imidazole-4-carboxamide hydrochloric acid salt dihydrate as a pale yellow crystal.

Reference Example 4

Under the nitrogen atmosphere, 10 g of 2-aminomalonamide and 35.4 mL of triethyl orthoformate were added to 200 mL of 2-propanol. After heating to 80° C., the reaction mixture was stirred for 13 hours at the same temperature. Color of the reaction liquid was pale blue when the reaction was completed. Subsequently, the reaction mixture was cooled to 58° C., then added with 10 mL of water followed by 8 mL of conc. hydrochloric acid. After cooling the reaction mixture to 5° C., the crystal was collected by filtration and then washed with 40 mL of acetone to give 16 g of 5-hydroxy-1H-imidazole-4-carboxamide hydrochloric acid salt dihydrate as a green crystal.

Example 4

Under the nitrogen atmosphere, 20.0 g of 5-hydroxy-1H-imidazole-4-carboxamide hydrochloric acid salt dihydrate prepared according to the method of Reference Example 2 was added to 240 mL of 0.45 mol/L hydrochloric acid and dissolved therein by heating to 50° C. At 50° C., 40 mL aqueous solution containing 14.3 g of sodium formate was added dropwise thereto over 35 minutes. The reaction mixture was cooled and stirred for 90 minutes with the inside temperature of 5° C. The crystal was collected by filtration and then washed with a mixture liquid containing 20 mL of acetone and 40 mL of water followed by 60 mL of acetone to give 12.6 g of 5-hydroxy-1H-imidazole-4-carboxamide.3/4 hydrate as a pale yellow crystal.

Figure 8:
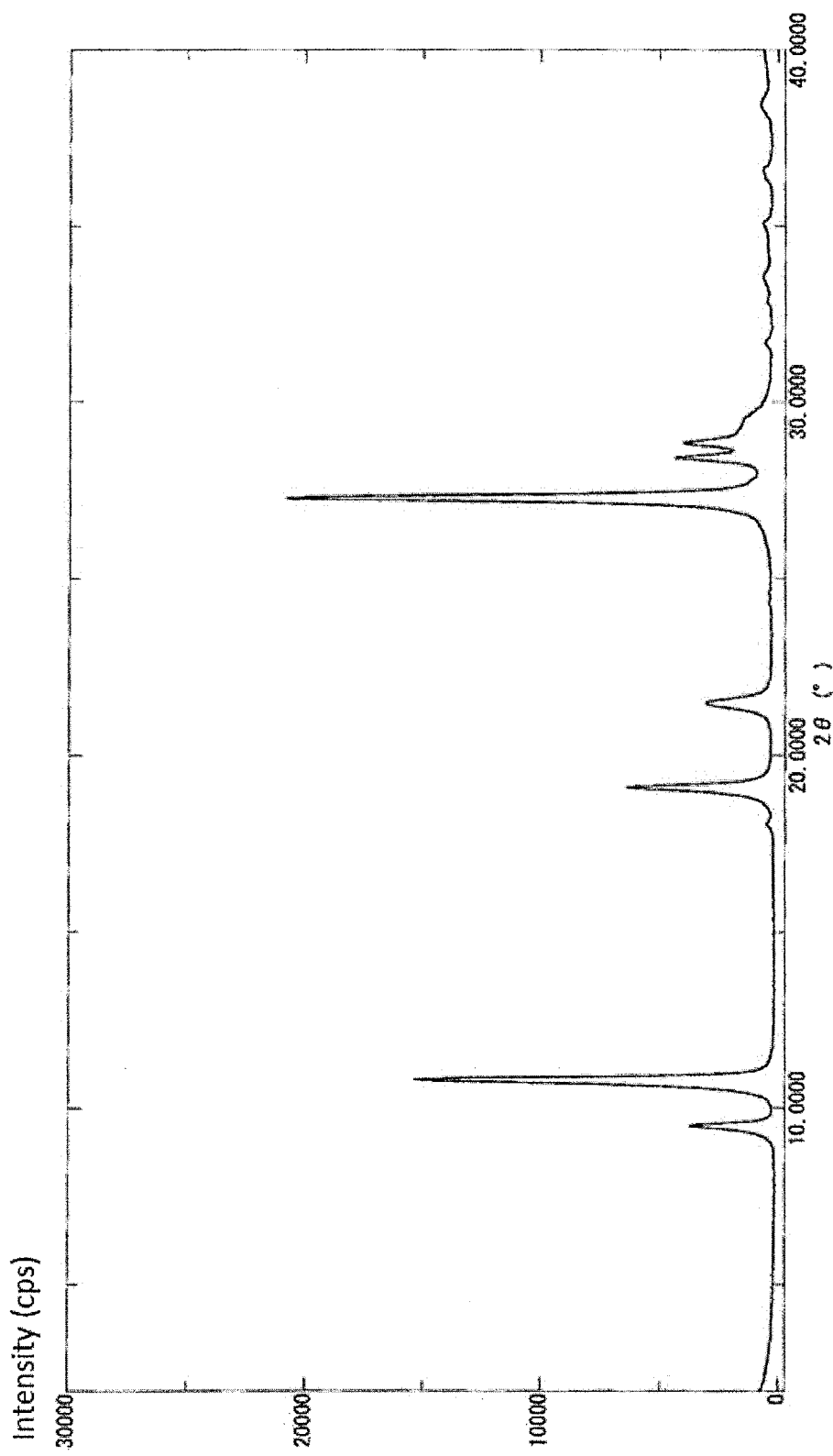
FIG. 8 is a drawing for illustrating one example of powder X ray diffraction pattern of the hydrate of the compound A.
Figure 9:
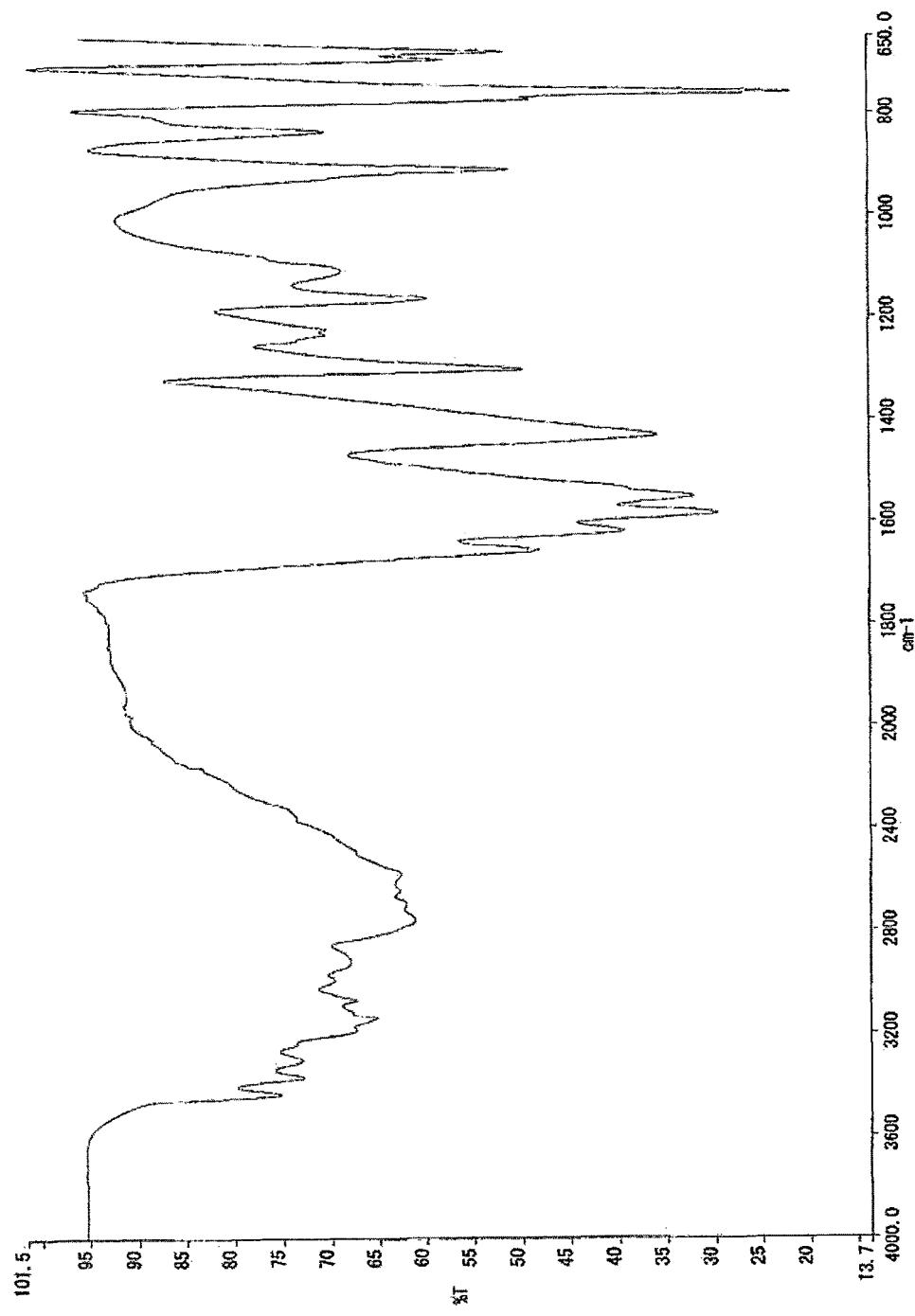
FIG. 9 is a drawing for illustrating one example of infrared absorption spectrum (ATR method) of the hydrate of the compound A.

Water content ratio: 8.6% (Karl Fischer Method)
IR (ATR) 1655, 1619, 1584, 1551 cm-1
Powder X-ray diffraction pattern is shown in FIG. 8 and Table 3 while the infrared absorption spectrum (ATR method) is shown in FIG. 9.

TABLE 3

| 2θ (°) | d Value (Å) | Relative intensity (%) |
|---|---|---|
| 9.5 | 9.3 | 17 |
| 10.8 | 8.2 | 69 |
| 19.1 | 4.7 | 30 |
| 21.5 | 4.1 | 14 |
| 27.2 | 3.3 | 100 |
| 28.4 | 3.1 | 21 |
| 28.8 | 3.1 | 20 |

Example 5

Under the nitrogen atmosphere, 20.0 g of 5-hydroxy-1H-imidazole-4-carboxamide hydrochloric acid salt dihydrate prepared according to the method of Reference Example 2 was added to 240 mL of 0.45 mol/L hydrochloric acid and dissolved therein by heating to 50° C. At 50° C., 40 mL aqueous solution containing 14.3 g of sodium formate was added dropwise thereto over 33 minutes. The reaction mixture was cooled. The crystal was collected by filtration and then washed with a mixture liquid containing 20 mL of acetone and 40 mL of water followed by 60 mL of acetone to give 12.8 g of 5-hydroxy-1H-imidazole-4-carboxamide.3/4 hydrate as a pale yellow crystal. The infrared absorption spectrum (ATR method) corresponds to that of Example 4.

Example 6

Under the nitrogen atmosphere, 1.5 g of 5-hydroxy-1H-imidazole-4-carboxamide hydrochloric acid salt dihydrate prepared according to the method of Reference Example 2 was added to 18 mL of 0.45 mol/L hydrochloric acid and dissolved therein by heating to 50° C. At 50° C., 6 mL aqueous solution containing 1.9 g of sodium formate was added dropwise thereto. pH of the reaction mixture was 3.1. The reaction mixture was cooled to room temperature. The crystal was collected by filtration and then washed with a mixture liquid containing 1.5 mL of acetone and 3.0 mL of water followed by 4.5 mL of acetone to give 0.90 g of 5-hydroxy-1H-imidazole-4-carboxamide.3/4 hydrate as a pale yellow crystal. The infrared absorption spectrum (ATR method) corresponded to that of Example 4.

Example 7

Under the nitrogen atmosphere, 10.0 g of 5-hydroxy-1H-imidazole-4-carboxamide hydrochloric acid salt dihydrate prepared according to the method of Reference Example 2 was added to 120 mL of 0.45 mol/L hydrochloric acid and dissolved therein by heating to 40 to 50° C. At 50° C., 25 mL aqueous solution containing 10.3 g of sodium acetate was added dropwise thereto. pH of the reaction mixture was 4.0.

After the dropwise addition was completed, the reaction solution was cooled to room temperature and stirred for 1 hour. The crystal was collected by filtration and then washed with a mixture liquid containing 10 mL of acetone and 20 mL of water followed by 30 mL of acetone to obtain 6.1 g of 5-hydroxy-1H-imidazole-4-carboxamide.3/4 hydrate as a gray crystal. The infrared absorption spectrum (ATR method) corresponds to that of Example 4.

Example 8

Under the nitrogen atmosphere, 1.5 g of 5-hydroxy-1H-imidazole-4-carboxamide hydrochloric acid salt dihydrate prepared according to the method of Reference Example 2 was added to 18 mL of 0.45 mol/L hydrochloric acid and dissolved therein by heating to 50° C. At 50° C., 6 mL aqueous solution containing 3.5 g of sodium malate was added dropwise thereto. pH of the reaction mixture was 2.6. The reaction mixture was cooled to room temperature. The crystal was collected by filtration and then washed with a mixture liquid containing 1.5 mL of acetone and 3.0 mL of water followed by 4.5 mL of acetone to give 0.89 g of 5-hydroxy-1H-imidazole-4-carboxamide.3/4 hydrate as a pale yellow crystal. The infrared absorption spectrum (ATR method) corresponds to that of Example 4.

Example 9

(1) Under the nitrogen atmosphere, 30 g of 2-aminomalonamide and 115 mg of oxalic acid were added to 600 mL of 2-propanol. After heating to 82° C., 106 mL of triethyl orthoformate was added dropwise to the mixture over 10 minutes. Subsequently, the reaction mixture was stirred for 7 hours and 30 minutes at 84° C. Subsequently, after cooling to 57° C., the reaction mixture was added with 30 mL of water followed by 24 mL of conc. hydrochloric acid. After cooling the reaction mixture to 5° C., the crystal was collected by filtration and then washed with 120 mL of acetone to give 49 g of 5-hydroxy-1H-imidazole-4-carboxamide hydrochloric acid salt dihydrate as a pale yellow crystal.

(2) Under the nitrogen atmosphere, 20.0 g of thus obtained 5-hydroxy-1H-imidazole-4-carboxamide hydrochloric acid salt dihydrate was added to 240 mL of 0.45 mol/L hydrochloric acid and dissolved therein by heating to 50° C. Thereafter, 40 mL aqueous solution containing 14.3 g of sodium formate was added dropwise thereto over 33 minutes. The reaction mixture was cooled to 5° C. The crystal was collected by filtration and then washed with a mixture liquid containing 20 mL of acetone and 40 mL of water followed by 60 mL of acetone to give 12.8 g of 5-hydroxy-1H-imidazole-4-carboxamide.3/4 hydrate as a pale yellow crystal.

The infrared absorption spectrum (ATR method) corresponds to that of Example 4.

Example 10

(1) Under the nitrogen atmosphere, 5.00 g of 2-aminomalonamide and 20 mg of formic acid were added to 80 mL of 2-propanol. After heating to 81° C., 17.7 mL of triethyl orthoformate was added to the mixture over 14 minutes. Subsequently, the reaction mixture was stirred for 6 hours and 33 minutes at 83° C. Subsequently, after cooling to 58° C., the reaction mixture was added dropwise with 5 mL of water followed by 4 mL of conc. hydrochloric acid. After cooling the mixture to 20° C., the crystal was collected by filtration and then washed with 20 mL of acetone to give 8.05 g of 5-hydroxy-1H-imidazole-4-carboxamide hydrochloric acid salt dihydrate as a yellow crystal.

(2) Under the nitrogen atmosphere, 2.00 g of thus obtained 5-hydroxy-1H-imidazole-4-carboxamide hydrochloric acid salt dihydrate was added to 22 mL of 0.45 mol/L hydrochloric acid and dissolved therein by heating to 46 to 48° C. After heating to 65° C., 2 mL of 0.45 mol/L hydrochloric acid was added. The solution was cooled to 50° C., and an aqueous solution prepared with 1.43 g of sodium formate and 4 mL of water was added dropwise thereto. The reaction mixture was cooled to 5° C. The crystal was collected by filtration and then washed with a mixture liquid containing 2 mL of acetone and 4 mL of water followed by 6 mL of acetone. After drying under the reduced pressure, 1.23 g of 5-hydroxy-1H-imidazole-4-carboxamide.3/4 hydrate was obtained as a brown crystal. The infrared absorption spectrum (ATR method) corresponds to that of Example 4.

Example 11

(1) Under the nitrogen atmosphere, 5.00 g of 2-aminomalonamide was added to 100 mL of 2-propanol. After heating to 80° C., 17.7 mL of triethyl orthoformate was added dropwise to the mixture over 30 minutes. Subsequently, the reaction mixture was stirred for 7 hours and 50 minutes at 83 to 84° C. Subsequently, after cooling to 50 to 60° C., the reaction mixture was added with an aqueous solution prepared with 4 mL of conc. hydrochloric acid and 5 mL of water. After cooling the mixture to 20 to 30° C., the crystal was collected by filtration and then washed with 25 mL of acetone to give 8.04 g of 5-hydroxy-1H-imidazole-4-carboxamide hydrochloric acid salt dihydrate as a pale yellow crystal.

(2) Under the nitrogen atmosphere, 5.00 g of thus obtained 5-hydroxy-1H-imidazole-4-carboxamide hydrochloric acid salt dihydrate was added to 50 mL of 0.5 mol/L hydrochloric acid and dissolved therein by heating to 48 to 49° C. To the resulting solution, an aqueous solution prepared with 4.11 g of sodium acetate and 10 mL of water was added dropwise over 18 minutes. The reaction mixture was cooled and the crystal was collected by filtration and then washed with a mixture liquid containing 5 mL of acetone and 10 mL of water followed by 15 mL of acetone. After drying under the reduced pressure, 3.21 g of 5-hydroxy-1H-imidazole-4-carboxamide-3/4 hydrate was obtained as a pale yellow crystal. The infrared absorption spectrum (ATR method) corresponds to that of Example 4.

Example 12

(1) Under the nitrogen atmosphere, 400 g of 5-hydroxy-1H-imidazole-4-carboxamide hydrochloric acid salt dihydrate prepared according to the method of Example 9 (1) was added to 4.40 L of 0.45 mol/L hydrochloric acid. After dissolving by heating to 57° C., 20.0 g of activated charcoal (TOKUSEI SHIRASAGI, manufactured by Japan Enviro-Chemicals, Ltd.) was added thereto and stirred for 45 minutes. The activated charcoal was removed by filtration and washed with 400 mL of 0.45 mol/L hydrochloric acid. The washing liquid was combined with the filtrate. The filtrate was cooled to 15° C. and stirred for 1 hour after added with 400 mL of conc. hydrochloric acid. The precipitated crystal was collected by filtration and then washed with 1.6 L of 2.4 mol/L hydrochloric acid followed by 1.60 L of acetone. By performing the drying under the reduced pressure, 364 g of 5-hydroxy-1H-imidazole-4-carboxamide hydrochloric acid salt dihydrate was obtained as a pale yellow crystal.

(2) Under the nitrogen atmosphere, 320 g of thus obtained 5-hydroxy-1H-imidazole-4-carboxamide hydrochloric acid salt dihydrate was added to 3.52 L of 0.45 mol/L hydrochloric acid and dissolved therein by heating to 57° C. The reaction solution was filtered and the residuals were washed with 320 mL of 0.45 mol/L hydrochloric acid. The washing liquid was combined with the reaction solution and adjusted to 50° C. Thereafter, an aqueous solution prepared with 229 g of sodium formate and 1.14 L of water was added dropwise thereto at 50° C. over 66 minutes. The reaction mixture was cooled to 10° C. or less and allowed to remain overnight. The precipitated crystal was collected by filtration and then washed with a mixture liquid containing 320 mL of acetone and 640 mL of water followed by 960 mL of acetone. After drying under the reduced pressure, 198 g of 5-hydroxy-1H-imidazole-4-carboxamide.3/4 hydrate was obtained as a pale yellow crystal. The infrared absorption spectrum (ATR method) corresponds to that of Example 4.

Example 13

(1) Under the nitrogen atmosphere, 7.00 g of 5-hydroxy-1H-imidazole-4-carboxamide hydrochloric acid salt dihydrate prepared according to the method of Example 10 (1) was added to 77 mL of 0.45 mol/L hydrochloric acid. After dissolving by heating to 60° C., 350 mg of activated charcoal (TOKUSEI SHIRASAGI, manufactured by Japan Enviro-Chemicals, Ltd.) was added thereto and stirred for 30 minutes at 60° C. The activated charcoal was removed by filtration and washed with 7 mL of 0.45 mol/L hydrochloric acid. The washing liquid was combined with the filtrate. The filtrate was cooled to 5 to 10° C. and stirred at 5 to 10° C. for 1 hour after added with 7 mL of conc. hydrochloric acid. The precipitated crystal was collected by filtration and then washed with 28 mL of 1.5 mol/L hydrochloric acid followed by 28 mL of acetone. By performing the drying under the reduced pressure, 6.44 g of 5-hydroxy-1H-imidazole-4-carboxamide hydrochloric acid salt dihydrate was obtained as a pale yellow crystal.

(2) Under the nitrogen atmosphere, 5.00 g of thus obtained 5-hydroxy-1H-imidazole-4-carboxamide hydrochloric acid salt dihydrate was added to 60 mL of 0.45 mol/L hydrochloric acid and dissolved therein by heating to 50° C. Thereafter, an aqueous solution prepared with 3.58 g of sodium formate and 20 mL of water was added dropwise thereto. The reaction mixture was cooled to 5° C. on an ice bath and stirred for 30 minutes. The precipitated crystal was collected by filtration and then washed with a mixture liquid containing 5 mL of acetone and 10 mL of water followed by 15 mL of acetone. After drying under the reduced pressure, 3.17 g of 5-hydroxy-1H-imidazole-4-carboxamide.3/4 hydrate was obtained as a pale yellow crystal. The infrared absorption spectrum (ATR method) corresponds to that of Example 4.

Example 14

(1) Under the nitrogen atmosphere, 7.00 g of 5-hydroxy-1H-imidazole-4-carboxamide hydrochloric acid salt dihydrate prepared according to the method of Reference Example 3 was added to 77 mL of 0.45 mol/L hydrochloric acid. After dissolving by heating to 60° C., 350 mg of activated charcoal (TOKUSEI SHIRASAGI, manufactured by Japan EnviroChemicals, Ltd.) was added thereto and stirred for 30 minutes at 60° C. The activated charcoal was removed by filtration and washed with 7 mL of 0.45 mol/L hydrochloric acid. The washing liquid was combined with the filtrate. The filtrate was cooled to 5 to 10° C. and stirred at 5 to 10° C. for 1 hour after added with 7 mL of conc. hydrochloric acid. The precipitated crystal was collected by filtration and then washed with 28 mL of 1.5 mol/L hydrochloric acid followed by 28 mL of acetone. By performing the drying under the reduced pressure, 6.44 g of 5-hydroxy-1H-imidazole-4-carboxamide hydrochloric acid salt dihydrate was obtained as a pale yellow crystal.

(2) Under the nitrogen atmosphere, 5.00 g of thus obtained 5-hydroxy-1H-imidazole-4-carboxamide hydrochloric acid salt dihydrate was added to 60 mL of 0.45 mol/L hydrochloric acid and dissolved therein by heating to 50° C. Thereafter, an aqueous solution prepared with 3.58 g of sodium formate and 20 mL of water was added dropwise thereto. The reaction mixture was cooled to 5° C. and stirred for 30 minutes. The precipitated crystal was collected by filtration and then washed with a mixture liquid containing 5 mL of acetone and 10 mL of water followed by 15 mL of acetone. After drying under the reduced pressure, 3.22 g of 5-hydroxy-1H-imidazole-4-carboxamide.3/4 hydrate was obtained as a pale yellow crystal. The infrared absorption spectrum (ATR method) corresponds to that of Example 4.

Comparative Example 2

Under the nitrogen atmosphere, 10.0 g of 2-aminomalonamide and 81.2 mg of p-toluene sulfonic acid monohydrate were added to 200 mL of 2-propanol. After heating to 82° C., 35.4 mL of triethyl orthoformate was added dropwise to the mixture over 5 minutes. Subsequently, the reaction mixture was stirred for 3 hours at 80° C. Color of the reaction liquid was deep blue when the reaction was completed. Subsequently, after cooling to 57° C., the reaction mixture was added with 10 mL of water followed by 8 mL of conc. hydrochloric acid. After cooling the reaction mixture to 5° C., the crystal was collected by filtration and then washed with 40 mL of acetone to give 15.6 g of 5-hydroxy-1H-imidazole-4-carboxamide hydrochloric acid salt dihydrate as a green crystal.

Comparative Example 3

Under the nitrogen atmosphere, 10.0 g of 2-aminomalonamide and 44 mg of sulfuric acid were added to 200 mL of 2-propanol. After heating to 80° C., 35.4 mL of triethyl orthoformate was added dropwise to the mixture over 10 minutes. Subsequently, the reaction mixture was stirred for 7 hours at 80° C. Color of the reaction liquid was deep blue when the reaction was completed. Subsequently, after cooling to 58° C., the reaction mixture was added with 10 mL of water followed by 8 mL of conc. hydrochloric acid. After cooling the reaction mixture to 5° C., the crystal was collected by filtration and then washed with 40 mL of acetone to give 15.6 g of 5-hydroxy-1H-imidazole-4-carboxamide hydrochloric acid salt dihydrate as a green crystal.

Comparative Example 4

(1) 100 g of 5-hydroxy-1H-imidazole-4-carboxamide prepared with reference to the method described in Example 9 of Patent Document 1 (International Publication No. 2009/035168) was added to 1456 g of 7% hydrochloric acid. After dissolving by heating to 75° C., 4.6 g of activated charcoal (TOKUSEI SHIRASAGI, manufactured by Japan Enviro- Chemicals, Ltd.) and 14 g of 7% hydrochloric acid were added thereto and stirred for 10 minutes at 75° C. The activated charcoal was removed by filtration and washed with 211 g of 7% hydrochloric acid. The washing liquid was combined with the filtrate. The filtrate was cooled to 20 to 25° C. and stirred for 1 hour. The precipitated crystal was collected by filtration and then washed with 314 mL of 2-propanol twice. By performing the drying under the reduced pressure, 133 g of 5-hydroxy-1H-imidazole-4-carboxamide hydrochloric acid salt dihydrate was obtained as a colorless crystal.

(2) Under the nitrogen atmosphere, 1.5 g of thus obtained 5-hydroxy-1H-imidazole-4-carboxamide hydrochloric acid salt dihydrate was added to 18 mL of 0.45 mol/L hydrochloric acid and dissolved therein by heating to 40 to 50° C. To the solution, 6 mL of aqueous solution containing 0.63 g of sodium hydroxide was added dropwise over 10 minutes. pH of the reaction mixture was 6.6. After the dropwise addition was completed, the reaction solution was cooled to room temperature and stirred for 1 hour. The crystal was collected by filtration and then washed with a mixture liquid containing 1.5 mL of acetone and 3.0 mL of water followed by 4.5 mL of acetone to give 0.52 g of 5-hydroxy-1H-imidazole-4-carboxamide.3/4 hydrate as a blue crystal.

Comparative Example 5

Under the nitrogen atmosphere, 5.0 g of 5-hydroxy-1H-imidazole-4-carboxamide hydrochloric acid salt dihydrate prepared according to the method of Comparative Example 4 (1) was added to 60 mL of 0.45 mol/L hydrochloric acid and dissolved therein by heating to 40 to 50° C. To the solution, 3.9 mL of 25% ammonia water was added dropwise over 10 minutes. pH of the reaction mixture was 6.6. After the dropwise addition was completed, the reaction solution was cooled to room temperature and stirred for 1 hour. The crystal was collected by filtration and then washed with a mixture liquid containing 5 mL of acetone and 10 mL of water followed by 15 mL of acetone to give 0.54 g of 5-hydroxy-1H-imidazole-4-carboxamide.3/4 hydrate as a blue crystal.

Comparative Example 6

With reference to the method described in Example 9 of Patent Document 1 (International Publication No. 2009/035168), 5-hydroxy-1H-imidazole-4-carboxamide was obtained as a pale yellow solid.

As a result of $^1$H-NMR analysis, it was found that the 5-hydroxy-1H-imidazole-4-carboxamide obtained contains about 0.15% of benzoic acid.

Comparative Example 7

(1) Under the nitrogen atmosphere, 20 g of 2-aminomalonamide and 325 mg of p-toluene sulfonic acid monohydrate were added to 400 mL of 2-propanol. After heating to 82° C., 56.7 mL of triethyl orthoformate was added in divided portions to the mixture over 4 hours and 8 minutes. Subsequently, the reaction mixture was stirred for 3 hours and 21 minutes at 79° C. Subsequently, after cooling to 51° C., the reaction mixture was added dropwise with 20 mL of water followed by 15.7 mL of conc. hydrochloric acid. After cooling the reaction mixture to room temperature, the crystal was collected by filtration and then washed with 100 mL of acetone to give 30.56 g of 5-hydroxy-1H-imidazole-4-carboxamide hydrochloric acid salt dihydrate as a gray crystal.

(2) Under the nitrogen atmosphere, 1 g of thus obtained 5-hydroxy-1H-imidazole-4-carboxamide hydrochloric acid salt dihydrate was added to 11 mL of 0.45 mol/L hydrochloric acid and dissolved therein by heating to 46 to 48° C. After heating to 65° C., 1 mL of 0.45 mol/L hydrochloric acid was added thereto. After cooling the resultant solution to 50° C., an aqueous solution containing 0.72 g of sodium formate and 2 mL of water was added dropwise thereto. The reaction mixture was cooled and the crystal was collected by filtration and then washed with a mixture liquid containing 1 mL of acetone and 2 mL of water followed by 3 mL of acetone. After performing the drying under the reduced pressure, 0.63 g of 5-hydroxy-1H-imidazole-4-carboxamide.3/4 hydrate was obtained as a brown crystal. The infrared absorption spectrum (ATR method) corresponds to that of Example 4.

Comparative Example 8

(1) Under the nitrogen atmosphere, 7.00 g of 5-hydroxy-1H-imidazole-4-carboxamide hydrochloric acid salt dihydrate prepared according to the method of Comparative Example 7 (1) was added to 77 mL of 0.45 mol/L hydrochloric acid. After dissolving therein by heating to 60° C., 350 mg of activated charcoal (TOKUSEI SHIRASAGI, manufactured by Japan EnviroChemicals, Ltd.) was added thereto and stirred for 30 minutes at 60° C. The activated charcoal was removed by filtration and washed with 7 mL of 0.45 mol/L hydrochloric acid. The washing liquid was combined with the filtrate. The filtrate was cooled to 5 to 10° C. and stirred at 5 to 10° C. for 1 hour after added with 7 mL of conc. hydrochloric acid. The precipitated crystal was collected by filtration and then washed with 28 mL of 1.5 mol/L hydrochloric acid followed by 28 mL of acetone. By performing the drying under the reduced pressure, 6.44 g of 5-hydroxy-1H-imidazole-4-carboxamide hydrochloric acid salt dihydrate was obtained as a pale yellow crystal.

(2) Under the nitrogen atmosphere, 5.00 g of thus obtained 5-hydroxy-1H-imidazole-4-carboxamide hydrochloric acid salt dihydrate was added to 60 mL of 0.45 mol/L hydrochloric acid and dissolved therein by heating to 50° C. Thereafter, an aqueous solution prepared with 3.58 g of sodium formate and 20 mL of water was added dropwise thereto. The reaction mixture was cooled to 5° C. and stirred for 30 minutes. The precipitated crystal was collected by filtration and then washed with a mixture liquid containing 5 mL of acetone and 10 mL of water followed by 15 mL of acetone. After drying under the reduced pressure, 3.21 g of 5-hydroxy-1H-imidazole-4-carboxamide.3/4 hydrate was obtained as a pale yellow crystal. The infrared absorption spectrum (ATR method) corresponds to that of Example 4.

Usefulness of the invention is explained in view of the following test examples.

Meanwhile, in each test example, the final compounds obtained from Reference Examples, Examples and Comparative Examples were used.

Test Example 2

Observation of the color of the reaction liquid of Reference Examples 2 to 4 and Comparative Examples 2 and 3 was made. The reaction liquids at the time of terminating the reaction are illustrated in FIGS. 12 to 16 and the results are given in Table 4.

TABLE 4

|  | Acidic compound | Color of reaction liquid |
|---|---|---|
| Reference Example 2 | Oxalic acid | Pale yellow |
| Reference Example 3 | — | Pale yellow |
| Reference Example 4 | — | Pale blue |
| Comparative Example 2 | p-Toluene sulfonic acid | Deep blue |
| Comparative Example 3 | Sulfuric acid | Deep blue |

Color of the reaction liquid of Reference Examples 2 and 3 was pale yellow. Meanwhile, color of the reaction liquid of Reference Example 4 was pale blue and color of the reaction liquid of Comparative Examples 2 and 3 was deep blue.

Thus, it was shown that, by carrying out the synthesis of the compound A in the absence of mineral acid and in the absence of sulfonic acid, coloration with blue color of the reaction liquid was inhibited.

Test Example 3

Observation of the color of the crystals obtained in Examples 5 and 8 and Comparative Examples 4 and 5 was made. The results are given in Table 5.

TABLE 5

|  | Salt | Color of crystals |
|---|---|---|
| Example 5 | Sodium formate | Pale yellow |
| Example 8 | Sodium malate | Pale yellow |
| Comparative Example 4 | Sodium hydroxide | Blue |
| Comparative Example 5 | Ammonia water | Blue |

Color of the reaction liquid of Examples 5 and 8 was pale yellow. Meanwhile, color of the reaction liquid of Comparative Examples 4 and 5 was blue.

Thus, it was shown that, the coloration with blue color was inhibited in the crystals obtained in Examples 5 and 8.

Test Example 4

As a test material, the compounds of Examples 9, 11 and 13 and also the compounds of Comparative Examples 6 and 7 were used.

About 1 g of the test material was added in a storage bag, the storage bag being prepared by inserting one polyethylene bag into another polyethylene bag, each polyethylene bag having a thickness of 0.04 mm, each of the polyethylene bags was sealed, and the test material was stored for 2 weeks in conditions of air atmosphere at a temperature of 40° C. and a relative humidity of 75%. Color change of the crystal before and after the test was evaluated based on color difference. The results are given in Table 6.

Colorimeter: Spectrophotometric colorimeter SE 2000, manufactured by NIPPON DENSHOKU INDUSTRIES CO., LTD.

Measurement method: Reflection method

TABLE 6

|  | Acidic compound | Salt | Color difference ($\Delta E$) |
|---|---|---|---|
| Example 9 | Oxalic acid | Sodium formate | 2.4 |
| Example 11 | — | Sodium acetate | 1.8 |
| Example 13 | Formic acid | Sodium formate | 5.1 |
| Comparative Example 6 | (Method described in Patent Document 1) | | 25.6 |
| Comparative Example 7 | p-Toluene sulfonic acid | Sodium formate | 8.8 |

The compound of Comparative Example 7 showed a smaller color difference compared to the compound of Comparative Example 6.

The compounds of Example 9, 11 and 13 showed a smaller color difference compared to the compounds of Comparative Examples 6 and 7.

Further, when observed with a naked eye, the compound of Example 9 showed no coloration with blue color even after it has been stored for 2 weeks in conditions of a temperature of 60° C. and a relative humidity of 75%.

Figure 10:
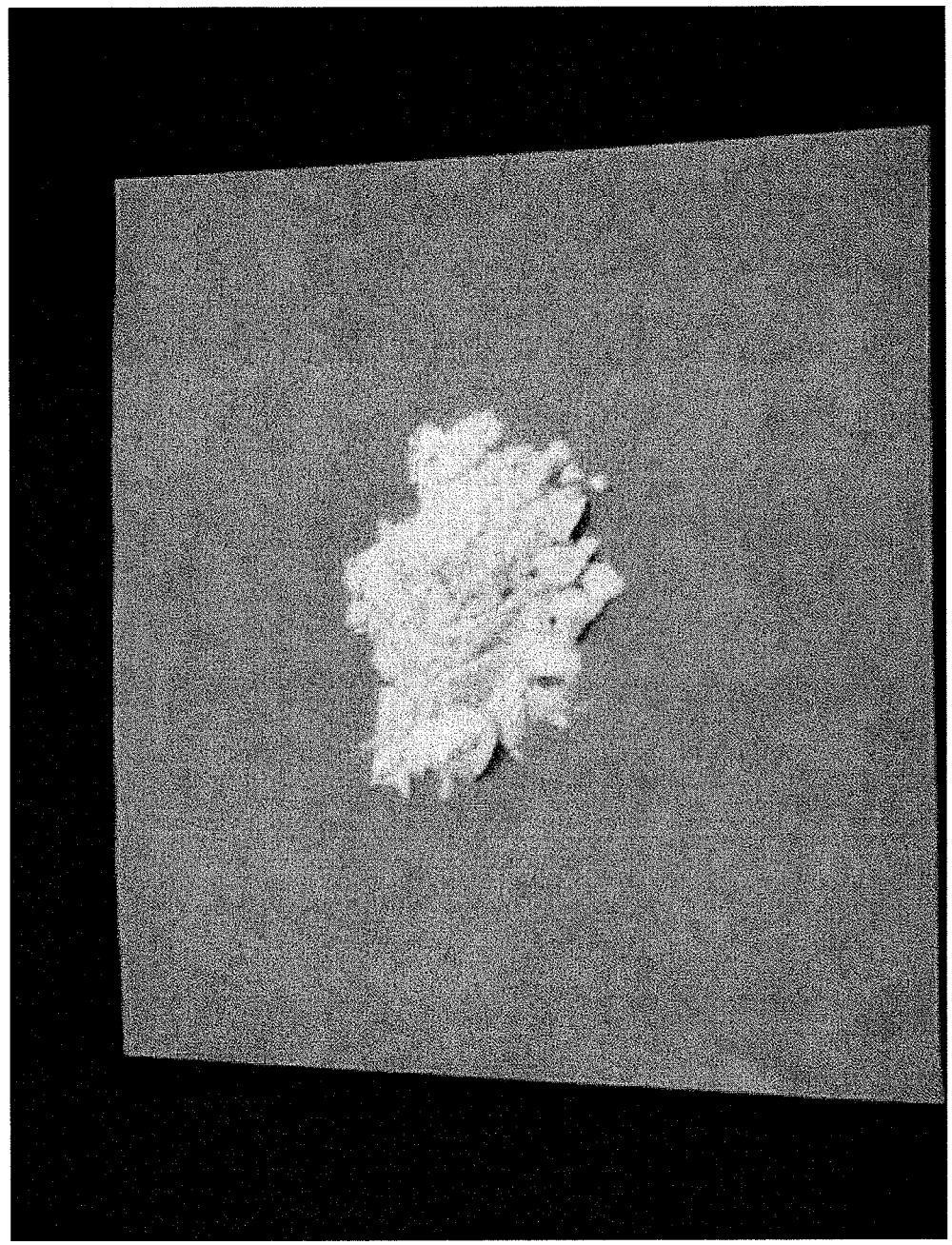
FIG. 10 is a photographic image of the hydrate of the compound A.

Compound of Example 9 before starting the test is illustrated in FIG. 10.

Figure 11:
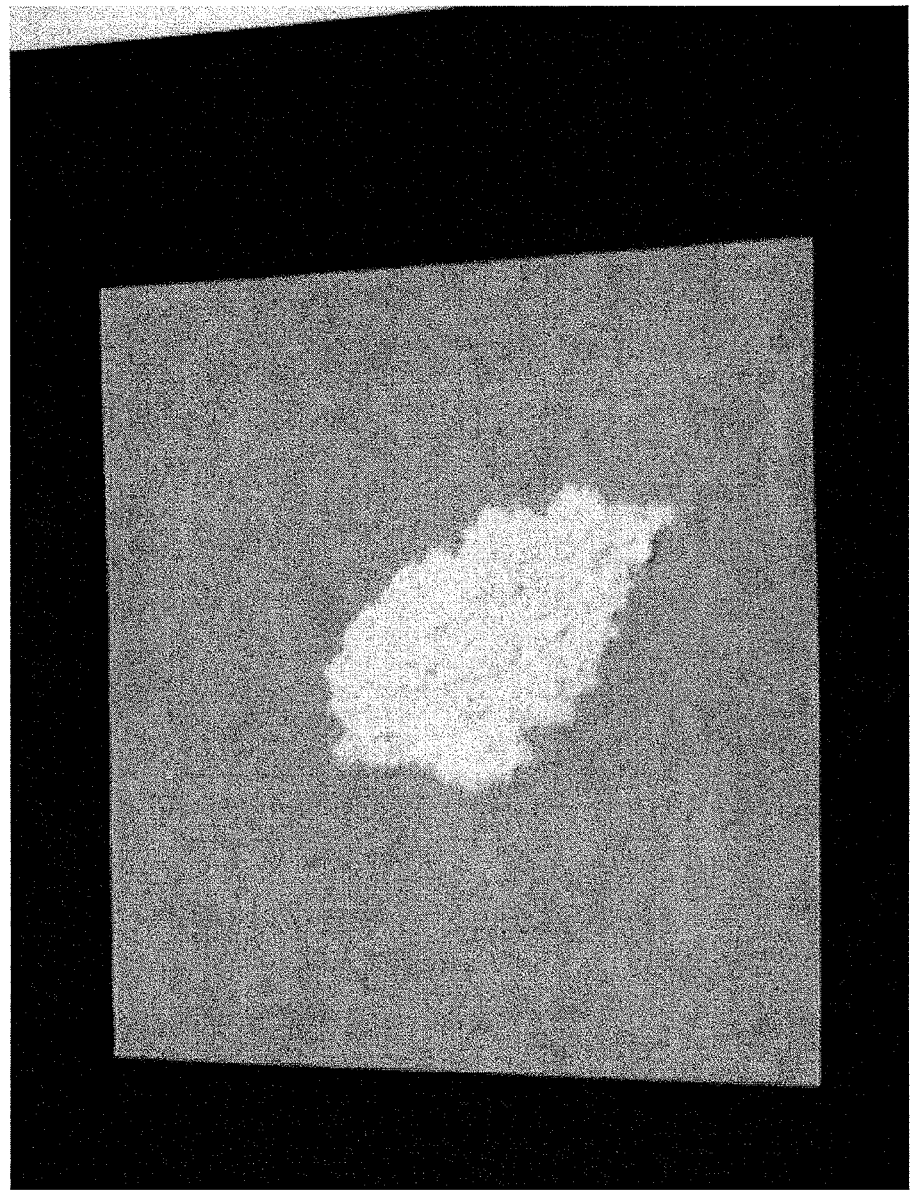
FIG. 11 is a photographic image illustrating the state of the hydrate of the compound A after it has been stored for 2 weeks in conditions of a temperature of 60° C. and a relative humidity of 75%.
Figure 12:
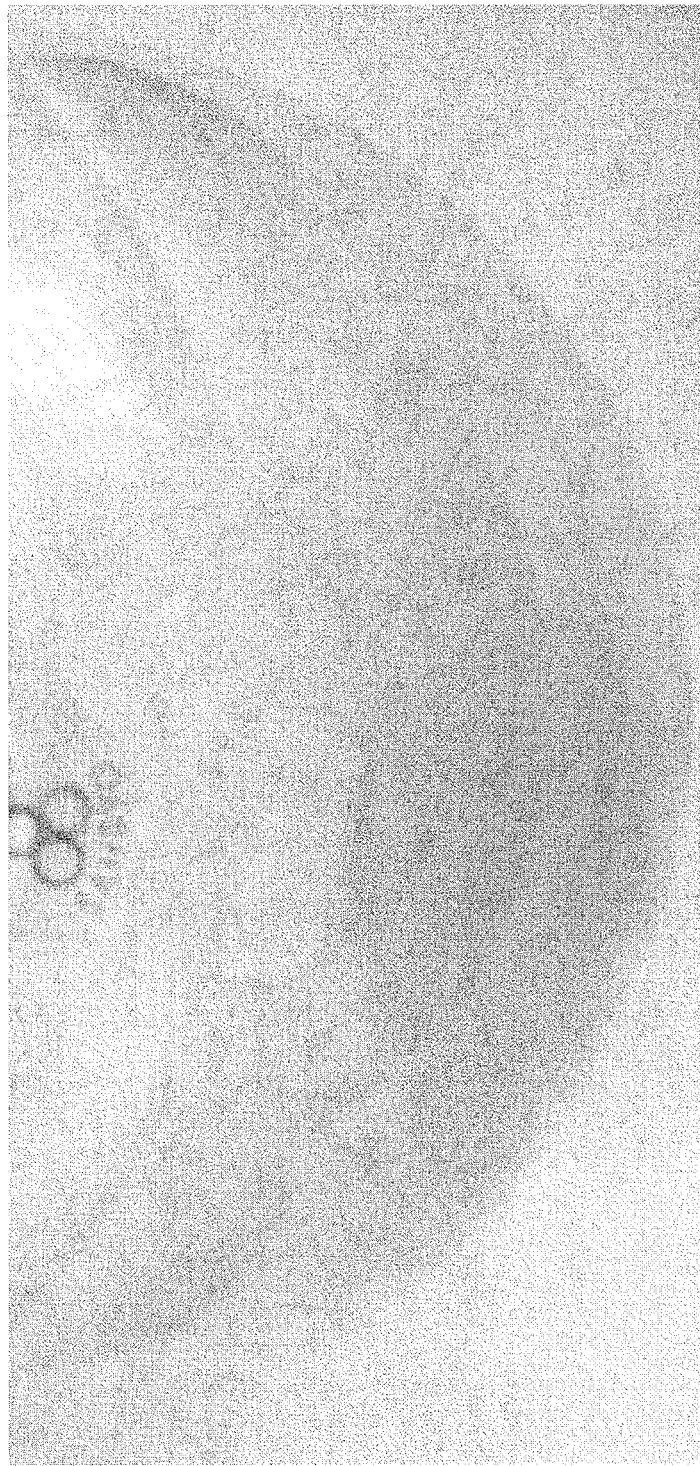
FIG. 12 is a photographic image illustrating the state of the reaction liquid when the reaction of Reference Example 2 is completed.
Figure 13:
FIG. 13 is a photographic image illustrating the state of the reaction liquid when the reaction of Reference Example 3 is completed.
Figure 14:
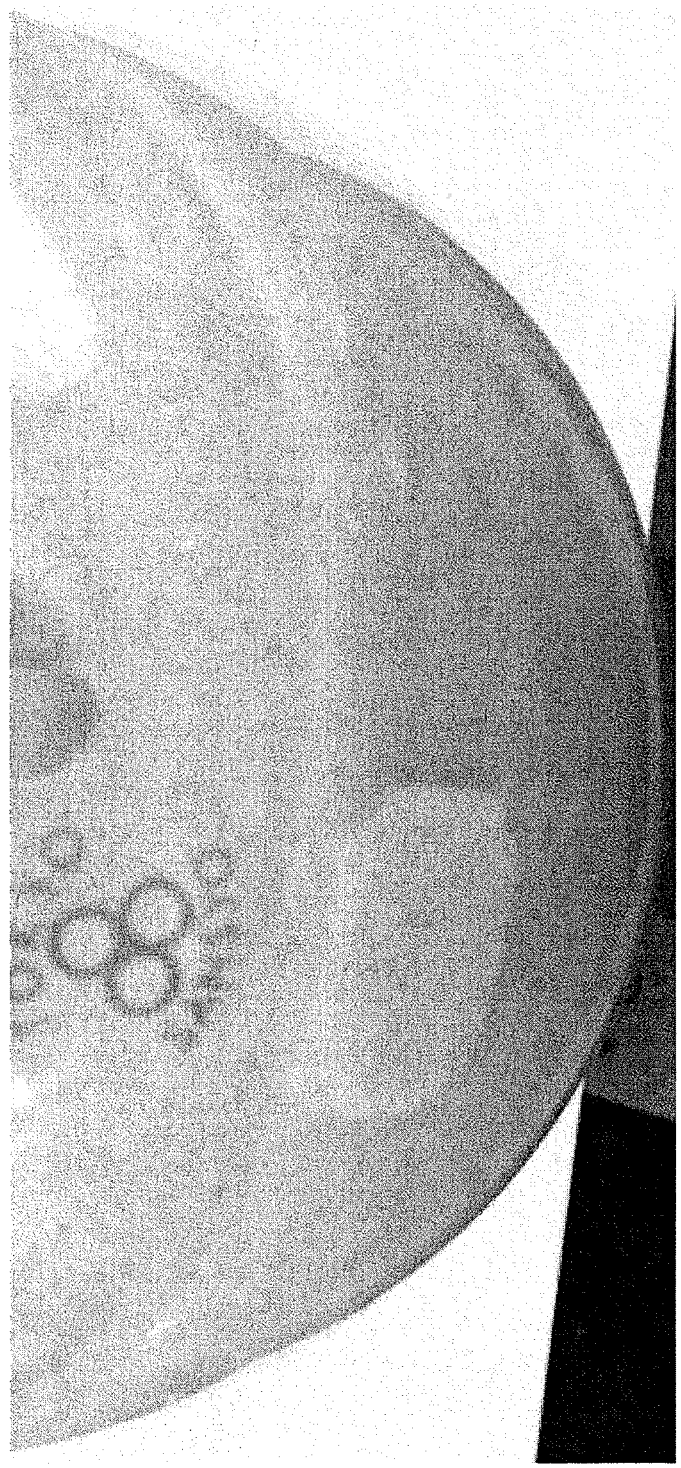
FIG. 14 is a photographic image illustrating the state of the reaction liquid when the reaction of Reference Example 4 is completed.
Figure 15:
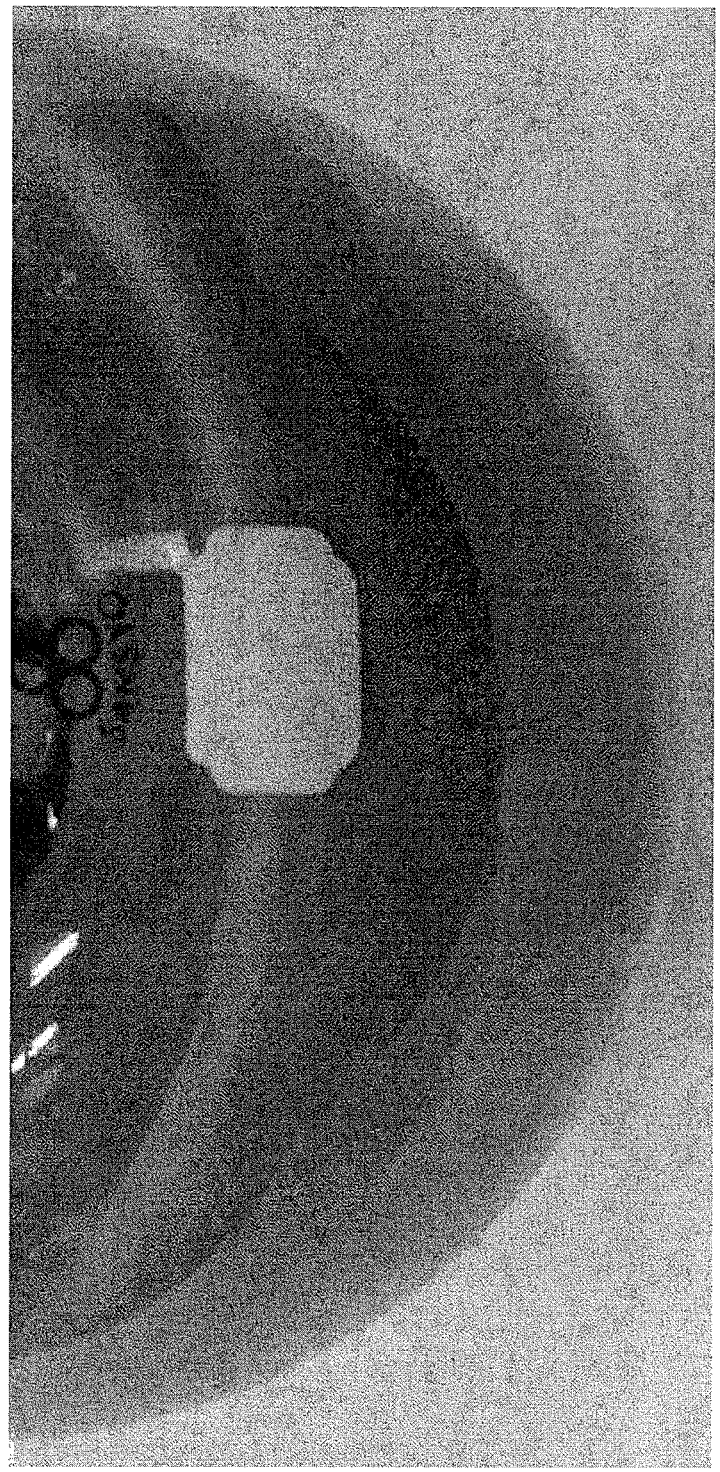
FIG. 15 is a photographic image illustrating the state of the reaction liquid when the reaction of Comparative Example 2 is completed.
Figure 16:
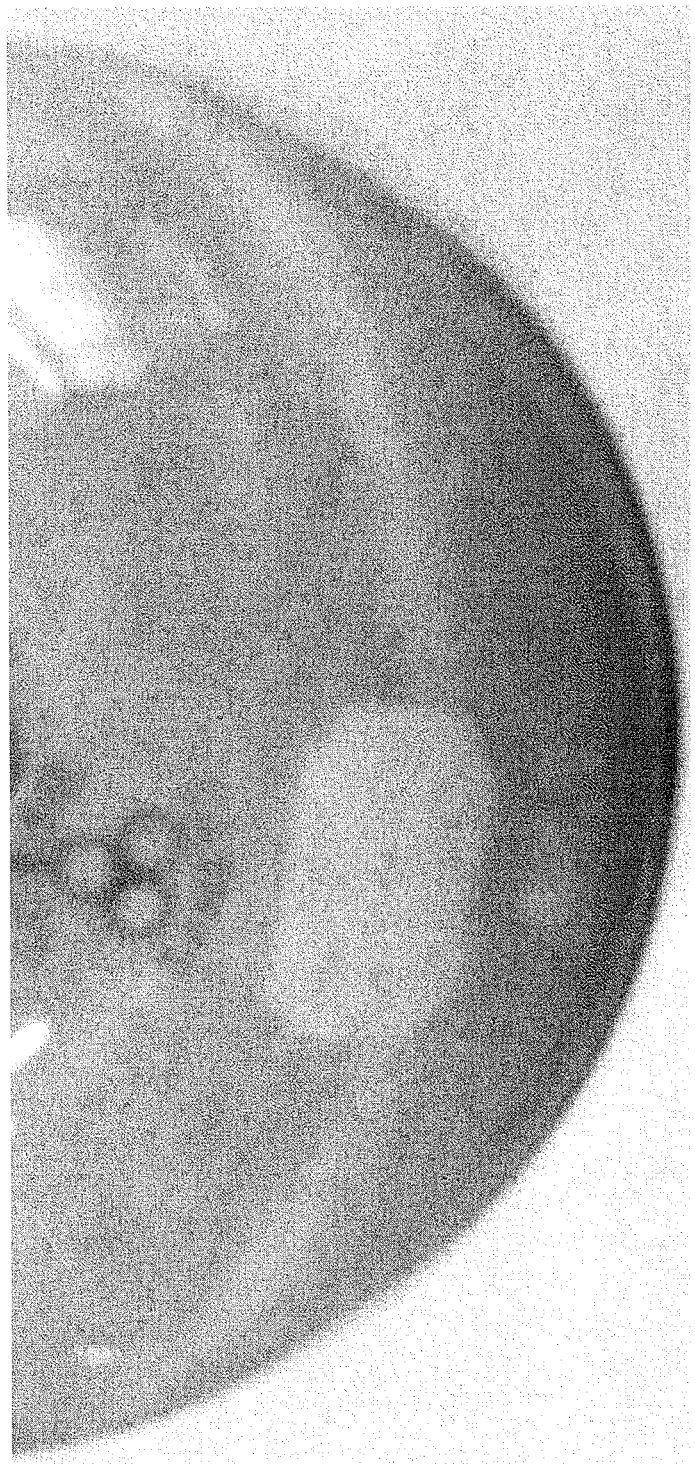
FIG. 16 is a photographic image illustrating the state of the reaction liquid when the reaction of Comparative Example 3 is completed.

Compound of Example 9 after it has been stored for 2 weeks under the condition including a temperature of 60° C. and a relative humidity of 75% is illustrated in FIG. 11.

The hydrate of the compound A that is obtained according to the production method of the invention has a small color difference between the crystal before storage and the crystal after storage, and has excellent storage stability.

Test Example 5

As a test material, the compound of Example 12 and also the compound of Comparative Example 8 were used.

About 1 g of the test material was added in a storage bag, the storage bag being prepared by inserting one polyethylene bag into another polyethylene bag, each polyethylene bag having a thickness of 0.04 mm, each of the polyethylene bags was sealed, and the test material was stored for 2 weeks in conditions of air atmosphere at a temperature of 40° C. and a relative humidity of 75%. Color change of the crystal before and after the test was evaluated based on color difference. The results are given in Table 7.

Colorimeter: Spectrophotometric colorimeter SE 2000, manufactured by NIPPON DENSHOKU INDUSTRIES CO., LTD.

Measurement method: Reflection method

TABLE 7

|  | Acidic compound | Salt | Color difference ($\Delta E$) |
|---|---|---|---|
| Example 12 | Oxalic acid | Sodium formate | 1.3 |
| Comparative Example 8 | p-Toluene sulfonic acid | Sodium formate | 6.5 |

Compound of Comparative Example 8 was prepared by using activated charcoal. However, it showed a huge color difference. Further, the compound of Comparative Example 8 showed poor storage stability compared to the compound of Example 12. Meanwhile, compound of Example 12 showed a small color difference.

The hydrate of the compound A that is obtained according to the production method of the invention has a small color difference between the crystal before storage and the crystal after storage, and has excellent storage stability.

Test Example 6

Hue (H) in the Munsell color system of the crystals of Examples 9, 11 to 14 was observed. The results are given in Table 8.

Colorimeter: Spectrophotometric colorimeter SE 2000, manufactured by NIPPON DENSHOKU INDUSTRIES CO., LTD.

Measurement method: Reflection method

TABLE 8

|  | Hue (H) |
|---|---|
| Example 9 | 3.1Y |
| Example 11 | 3.8Y |
| Example 12 | 4.4Y |
| Example 13 | 5.9Y |
| Example 14 | 5.9Y |

INDUSTRIAL APPLICABILITY

The crystal of the present invention has at least one of the following characteristics; (1) it does not contain additives, (2) it can be stored for a long period of time as there is no deterioration such as coloration even under high temperature and high humidity conditions, (3) it has little impurities, (4) it has easy handlability, (5) it is produced by using a solvent safe for a human body, (6) it is produced under the conditions with low environmental burdens, and (7) it can be produced in large scale, and it is useful as an original drug substance of a pharmaceutical.

The production method according to the invention is very useful as a method for industrial production of 5-hydroxy-1H-imidazole-4-carboxamide.3/4 hydrate in that (1) it does not contain additives, (2) a color difference between the crystal before storage and the crystal after storage is small, (3) it is excellent in storage stability, and (4) it has little impurities.

The invention claimed is:

1. A crystal of 5-hydroxy-1H-imidazole-4-carboxamide hydrate, wherein the crystal has diffraction peaks at diffraction angles of 8.1, 12.6, 17.1, 19.3, 20.3 and 21.6°, represented by 2θ in a powder X-ray diffraction pattern.

2. A pharmaceutical composition containing a crystal of 5-hydroxy-1H-imidazole-4-carboxamide hydrate, wherein the crystal has diffraction peaks at diffraction angles of 8.1, 12.6, 17.1, 19.3, 20.3 and 21.6°, represented by 2θ in a powder X-ray diffraction pattern.

* * * * *